US009529258B2

(12) United States Patent
Noda et al.

(10) Patent No.: US 9,529,258 B2
(45) Date of Patent: Dec. 27, 2016

(54) ENERGY-SENSITIVE RESIN COMPOSITION

(71) Applicant: TOKYO OHKA KOGYO CO., LTD., Kawasaki-shi (JP)

(72) Inventors: Kunihiro Noda, Kawasaki (JP); Hiroki Chisaka, Kawasaki (JP); Dai Shiota, Kawasaki (JP); Kazuya Someya, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 14/758,199

(22) PCT Filed: Dec. 25, 2013

(86) PCT No.: PCT/JP2013/084649
§ 371 (c)(1),
(2) Date: Jun. 26, 2015

(87) PCT Pub. No.: WO2014/104090
PCT Pub. Date: Jul. 3, 2014

(65) Prior Publication Data
US 2015/0338734 A1 Nov. 26, 2015

(30) Foreign Application Priority Data

Dec. 28, 2012 (JP) .................................. 2012-288708

(51) Int. Cl.
G03F 7/004 (2006.01)
G03F 7/16 (2006.01)
G03F 7/20 (2006.01)
G03F 7/32 (2006.01)
G03F 7/40 (2006.01)
C07D 233/60 (2006.01)
C07C 323/47 (2006.01)
C07D 209/86 (2006.01)
C08K 5/33 (2006.01)
G03F 7/038 (2006.01)
C09D 179/08 (2006.01)
C08G 73/10 (2006.01)
C07D 233/56 (2006.01)
C08K 5/34 (2006.01)

(52) U.S. Cl.
CPC .......... *G03F 7/0041* (2013.01); *C07C 323/47* (2013.01); *C07D 209/86* (2013.01); *C07D 233/60* (2013.01); *C08G 73/105* (2013.01); *C08G 73/1042* (2013.01); *C08G 73/1067* (2013.01); *C08G 73/1071* (2013.01); *C08G 73/1078* (2013.01); *C08K 5/33* (2013.01); *C09D 179/08* (2013.01); *G03F 7/0045* (2013.01); *G03F 7/0387* (2013.01); *G03F 7/16* (2013.01); *G03F 7/20* (2013.01); *G03F 7/32* (2013.01); *G03F 7/40* (2013.01); *C07D 233/56* (2013.01); *C08K 5/34* (2013.01)

(58) Field of Classification Search
CPC ........ G03F 7/038; G03F 7/004; G03F 7/0045; G03F 7/32; G03F 7/20; G03F 7/40; C07D 233/60; C07D 209/86; C08G 73/1042; C08G 73/105; C08G 73/1067; C08G 73/1071; C08G 73/1078
USPC .............................................. 430/270.1, 325
See application file for complete search history.

(56) References Cited

U.S. PATENT DOCUMENTS

2011/0086311 A1    4/2011  Katayama et al.
2011/0267714 A1*  11/2011  Makino ................ C07D 209/86
                                                        359/892

FOREIGN PATENT DOCUMENTS

| JP | 2007-056196 | 3/2007 | |
| JP | 2007-249013 | 9/2007 | |
| JP | 2009-019113 | 1/2009 | |
| JP | 2010-106233 | 5/2010 | |
| JP | 2013-080206 | 5/2013 | |
| JP | 2013083934 A * | 5/2013 | ............. G03F 7/004 |
| WO | WO 2012064631 A1 * | 5/2012 | ........... C07D 213/75 |
| WO | WO 2012176693 A1 * | 12/2012 | ........... C07C 231/02 |
| WO | WO 2012176694 A1 * | 12/2012 | ........... C09B 23/143 |

OTHER PUBLICATIONS

Machine translation of JP 2007-294013 (no date).*
Machine translation Jp2007-056196 (no date).*

* cited by examiner

*Primary Examiner* — Amanda C Walke
(74) *Attorney, Agent, or Firm* — Knobbe Martens Olson & Bear LLP

(57) ABSTRACT

The present invention provides an energy-sensitive resin composition, a method of manufacturing a polyimide film or a polyimide molded product in which said composition is used, and a method of forming a pattern in which said composition is used. The composition supplies a polyimide resin exhibiting exceptional thermal resistance and low permittivity even by a heat treatment at a low temperature. The composition contains polyamic acid obtained by reacting tetracarboxylic dianhydride and diamine, a solvent, and a compound (A) decomposing by the action of light and/or heat and generating a base and/or an acid. The method of manufacturing a polyimide film or a polyimide molded product includes forming a coating film or molded product comprising the composition and decomposing the compound (A) in the film or product through exposure or heating. The method of forming a pattern sequentially includes forming, selectively exposing, developing and heating the film or product.

11 Claims, No Drawings

ENERGY-SENSITIVE RESIN COMPOSITION

CROSS-REFERENCE TO RELATED APPLICATIONS

This application is the U.S. National Phase under 35 U.S.C. §371 of International Application PCT/JP2013/084649, filed Dec. 25, 2013, which claims priority to JP 2012-288708, filed Dec. 28, 2012.

TECHNICAL FIELD

The present invention relates to an energy-sensitive resin composition comprising polyamic acid, a method of manufacturing a polyimide film or polyimide molded product using the energy-sensitive resin composition, and a method of forming a pattern using the energy-sensitive resin composition.

BACKGROUND ART

Since a polyimide resin has characteristics such as superior heat resistance, mechanical strength and insulation property or low dielectric constant, a polyimide resin is used widely as an insulating material or protective material in electric or electronic parts including various elements or electronic substrates such as multilayered wiring board. Also, in order to insulate or protect a minute point selectively in precision electric or electronic parts, polyimide resin which has been provided with patterning to a desired shape is used.

Generally, a polyimide resin is formed by subjecting polyamic acid obtained by polymerizing a tetracarboxylic dianhydride component and a diamine component in a polar organic solvent to heat treatment at a temperature of approximately 300° C. Therefore, polyimide products for an electronic material are often supplied as a solution of a polyimide precursor, such as polyamic acid. In producing electric or electronic parts, a solution of a polyimide precursor is supplied to a site where an insulating material or protective material is to be formed by a method such as coating or injection, etc. and thereafter the solution of the polyimide precursor is subjected to heat treatment at a high temperature of approximately 300° C. to form the insulating material or protective material.

Conventional methods for forming an insulating material or protective material made of a polyimide resin from a polyimide precursor have problems in which such conventional methods are not applicable to material which is weak to heat, because the conventional methods require heat treatment at a high temperature. Accordingly, a polyimide precursor composition which is capable of forming a polyimide resin by the treatment at a low temperature, i.e., approximately 200° C., has been developed (for example, Patent Document 1).

Patent Document 1: Japanese Unexamined Patent Application, Publication No. 2009-19113

DISCLOSURE OF THE INVENTION

Problems to be Solved by the Invention

However, in a case where a polyimide resin is formed at a low temperature, there is a problem such that the heat resistance of an obtained polyimide resin is damaged or the dielectric constant increases.

The present invention has been made in consideration of such a conventional situation and aims to provide an energy-sensitive resin composition which provides a polyimide resin which is excellent in heat resistance and has a low dielectric constant even when the heat treatment is performed at a low temperature; a method of manufacturing a polyimide film or polyimide molded product by using the energy-sensitive resin composition; and a method of forming a pattern using the energy-sensitive resin composition.

Means for Solving the Problems

The present inventors conducted intensive research to solve the problem. As a result, the inventors found that the aforementioned problem can be solved by adding a compound which decomposes by the action of at least one of light and heat and generates at least one of a base and an acid to a composition comprising polyamic acid, and came to complete the present invention. Specifically, the present invention provides the following.

The first aspect of the present invention is an energy-sensitive resin composition comprising polyamic acid obtained by reacting tetracarboxylic dianhydride with diamine, a solvent, and a compound (A) which decomposes by the action of at least one of light and heat and generates at least one of a base and an acid.

The second aspect of the present invention is a method of manufacturing a polyimide film or a polyimide molded product, comprising:

a forming step of forming a coating film or a molded product comprising the energy-sensitive resin composition; and a decomposing step of decomposing the compound (A) contained in the coating film or the molded product by exposing or heating the coating film or the molded product.

In a case where the compound (A) is a compound which decomposes by the action of at least light and generates at least one of a base and an acid, the third aspect of the present invention is a method of forming a pattern, wherein the method comprises:

a forming step of forming a coating film or a molded product comprising the energy-sensitive resin composition;

an exposure step of exposing the coating film or the molded product selectively;

a development step of developing the coating film or the molded product after the exposing; and a heating step of heating the coating film or the molded product after the developing.

Effects of the Invention

According to the present invention, it is possible to provide an energy-sensitive resin composition which provides a polyimide resin which is excellent in heat resistance and has a low dielectric constant even when the heat treatment is performed at a low temperature, a method of manufacturing a polyimide film or a polyimide molded product by using the energy-sensitive resin composition, and a method of forming a pattern using the energy-sensitive resin composition.

PREFERRED MODE FOR CARRYING OUT THE INVENTION

Energy-Sensitive Resin Composition

The energy-sensitive resin composition according to the present invention comprises at least polyamic acid obtained by reacting tetracarboxylic dianhydride with diamine, a solvent and a compound (A) which decomposes by the action of at least one of light and heat and generates at least one of a base and an acid.

Polyamic Acid

In the present invention, polyamic acid is not particularly limited and can be appropriately selected from the polyamic acids which are conventionally known as a precursor of polyimide resin. Polyamic acids can be used alone or as a mixture of two or more.

As a preferred polyamic acid, polyamic acid represented by the following formula (1) can be exemplified.

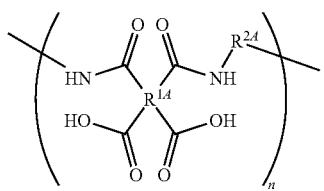

(1)

(In the formula (1), $R^{1A}$ is a tetravalent organic group; $R^{2A}$ is a divalent organic group; and n is the number of repetitions of the constituent unit represented in the parentheses.)

In the formula (1), $R^{1A}$ is a tetravalent organic group and $R^{2A}$ is a divalent organic group and the number of carbon atoms of these organic groups is preferably 2 to 50, and more preferably 2 to 30. Each of $R^{1A}$ and $R^{2A}$ can be either an aliphatic group, an aromatic group, or a group with a combination of these structures. $R^{1A}$ and $R^{2A}$ can include a halogen atom, an oxygen atom, and a sulfur atom in addition to a carbon atom and a hydrogen atom. In a case in which $R^{1A}$ and $R^{2A}$ include an oxygen atom, a nitrogen atom or a sulfur atom, the oxygen atom, the nitrogen atom or the sulfur atom can be included in $R^{1A}$ and $R^{2A}$ as a group selected from: a nitrogen-containing heterocyclic group; —CONH—; —NH—; —N=N—; —CH=N—; —COO—; —O—; —CO—; —SO—; —SO$_2$—; —S—; and —S—S—, and more preferably included in $R^{1A}$ and $R^{2A}$ as a group selected from: —O—; —CO—; —SO—; —SO$_2$—; —S—; and —S—S—.

The polyimide resin represented by the following formula (2) is obtained by ring closure of a polyamic acid represented by the aforementioned formula (1), by means of heating or a catalyst.

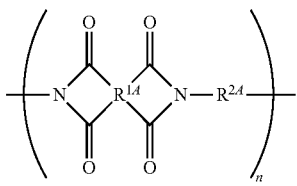

(2)

wherein, $R^{1A}$ and $R^{2A}$ are as defined for formula (1) and n is the number of repeating unit of the constituting unit represented in the parentheses.

The polyamic acid represented by the formula (1) can be obtained by reacting tetracarboxylic dianhydride with diamine in a solvent. Tetracarboxylic dianhydride and diamine which are raw materials for the synthesis of polyamic acids are not particularly limited as long as they can generate a polyamic acid by the reaction between an acid anhydride group and an amino group.

Amounts of the tetracarboxylic dianhydride and the diamine to be used upon synthesis of the polyamic acid are not particularly limited; however, it is preferable to use 0.50 to 1.50 moles, and more preferable to use 0.60 to 1.30 moles, and particularly preferable to use 0.70 to 1.20 moles of the diamine with respect to 1 mole of the tetracarboxylic dianhydride.

The tetracarboxylic dianhydride can be appropriately selected from tetracarboxylic dianhydrides which are conventionally used as a synthesis material for the polyamic acid. The tetracarboxylic dianhydride can be either an aromatic tetracarboxylic dianhydride or an aliphatic tetracarboxylic dianhydride; however, an aromatic tetracarboxylic dianhydride is preferable, from the respect of heat resistance of the resulting polyimide resin. The tetracarboxylic dianhydride can be used either singly or in combination of two or more.

Specific examples of preferred aromatic tetracarboxylic dianhydride include: pyromellitic dianhydride; 3,3',4,4'-biphenyl tetra carboxylic dianhydride; 2,3,3',4'-biphenyl tetra carboxylic dianhydride; 3,3',4,4'-benzophenone tetra carboxylic dianhydride; 4,4'-oxydiphthalic anhydride; and 3,3', 4,4'-diphenyl sulfone tetra carboxylic dianhydride; and the like. Among these, 3,3',4,4'-biphenyltetracarboxylic dianhydride and pyromellitic dianhydride are preferable from the viewpoint of price, availability, and the like.

Incidentally, in synthesizing polyamic acid, it is possible to use dicarboxylic anhydride in combination with tetracarboxylic dianhydride. Upon using these carboxylic anhydrides in combination, characteristics of the resulting polyimide resins may sometimes improve. Examples of the dicarboxylic anhydride include maleic anhydride, succinic anhydride, itaconic anhydride, phthalic anhydride, tetrahydrophthalic anhydride, hexahydrophthalic anhydride, methylendomethylenetetrahydrophthalic anhydride, chlorendic anhydride, methyltetrahydrophthalic anhydride, anhydrous glutaric acid, cis-4-cyclohexene-1,2-dicarboxylic anhydride and the like.

Diamines can be appropriately selected from diamines which are conventionally used as a synthesis material for the polyamic acid. The Diamine can be either an aromatic diamine or an aliphatic diamine; however, an aromatic diamine is preferable from the standpoint of heat resistance of the resulting polyimide resin. The diamine can be used in combination of two or more.

Specific examples of preferred aromatic diamine include: p-phenylenediamine; m-phenylenediamine; 2,4-diamino toluene; 4,4'-diamino biphenyl; 4,4'-diamino-2,2'-bis(trifluoromethyl)biphenyl; 3,3'-diaminodiphenyl sulfone; 4,4'-diaminodiphenyl sulfone; 4,4'-diaminodiphenyl sulfide; 4,4'-diaminodiphenylmethane; 4,4'-diamino diphenyl ether; 3,4'-diamino diphenyl ether; 3,3'-diamino diphenyl ether; 1,4-bis(4-aminophenoxy)benzene; 1,3-bis(4-aminophenoxy)benzene; 1,3-bis(3-aminophenoxy)benzene; 4,4'-bis(4-aminophenoxy) biphenyl; bis[4-(4-aminophenoxyl)phenyl]sulfone; bis[4-(3-aminophenoxyl)phenyl]sulfone; 2,2-bis[4-(4-aminophenoxyl)phenyl]propane; 2,2-bis[4-(4-aminophenoxyl)phenyl]hexafluoropropane; 9,9-bis(4-aminophenyl)fluorene, 9,9-bis(4-amino-3-methylphenyl)fluorene and 4,4'-[1,4-phenylenebis(1-methylethane-1,1-diyl)]dianiline and the like. Among these, p-phenylenediamine, m-phenylenediamine, 2,4-diamino toluene, and 4,4'-diamino diphenyl ether are preferable from the viewpoint of price, availability, and the like.

The reaction between tetracarboxylic dianhydride and diamine is generally performed in an organic solvent. The organic solvent used for the reaction of tetracarboxylic dianhydride and diamine is not particularly limited, as long as the solvent can dissolve the tetracarboxylic dianhydride and the diamine and does not react with the tetracarboxylic dianhydride or the diamine. The organic solvent may be used alone or in combination of two or more.

Examples of the organic solvent used for the reaction of tetracarboxylic dianhydride and diamine include nitrogen-containing polar solvents such as N-methyl-2-pyrrolidone, N,N-dimethylacetamide, N,N-diethyl acetamide, N,N-dimethylformamide, N,N-diethylformamide, N-methylcaprolactam and N,N,N',N'-tetramethyl urea, etc.; lactone-based polar solvents such as β-propiolactone, γ-butyrolactone, γ-valerolactone, δ-valerolactone, γ-caprolactone and ε-caprolactone, etc.; dimethyl sulfoxide; acetonitrile; fatty acid esters such as ethyl lactate and butyl lactate, etc.; and ethers such as diethyleneglycol dimethyl ether, diethyleneglycol diethyl ether, dioxane, tetrahydrofuran, methyl cellosolve acetate and ethyl cellosolve acetate, etc.

Among these organic solvents, preferred are nitrogen-containing polar solvents including N-methyl-2-pyrrolidone, N,N-dimethylacetamide, N,N-diethyl acetamide, N,N-dimethylformamide, N,N-diethylformamide, N-methylcaprolactam and N,N,N',N'-tetramethylurea, etc. for solubilities of the resulting polyamic acid or polyimide resins. Solvent The energy-sensitive resin composition according to the present invention comprises a solvent from the perspective of application characteristics and may be in a state of a paste containing a solid or in a state of a solution, and preferably in a state of a solution. The solvent may be used alone or in combination of two or more. There is no particular limitation for the type of solvent as long as it does not interfere with the object of the present invention. Preferred examples of the solvent are the same as the examples of the solvent used in the reaction between tetracarboxylic dianhydride and diamine. The solvent may include an alcohol solvent such as polyethylene glycol, ethylene glycol, diethylene glycol, propylene glycol, and dipropylene glycol, etc. When the solvent includes an alcohol-based solvent, a pattern which is good in heat resistance is likely to be formed.

The content of a solvent in the energy-sensitive resin composition is not particularly limited, within a range that does not inhibit objects of the present invention. The content of a solvent in the energy-sensitive resin composition is appropriately adjusted depending upon the solid content in the energy-sensitive resin composition. The solid content of the energy-sensitive resin composition is preferably between 5% and 50% by mass, and more preferably between 10% to 30% by mass.

Compound (A) which Decomposes by the Action of at Least One of Light and Heat and Generates at Least One of a Base and an Acid The energy-sensitive resin composition according to the present invention comprises a compound (A) which decomposes by the action of at least one of light and heat and generates at least one of a base and an acid. The compound (A) can be used either alone or in combination of two or more.

The compound (A) in the energy-sensitive resin composition according to the present invention decomposes and generates at least one of a base and an acid by exposing or heating the composition. The thus generated base or acid acts as an imidation catalyst to promote ring closure of polyamic acid in the energy-sensitive resin composition. The energy-sensitive resin composition according to the present invention can yield polyimide resin having excellent heat resistance and a low dielectric constant by containing the compound (A), even when the heat treatment is performed at a low temperature.

The compound (A) is preferably a compound which decomposes at 120 to 180° C. and generates a base. Such a compound (A) decomposes by heating and generates a base, even when it is heated at a low temperature, such as 220° C. or lower, as long as the heating temperature is equal to or higher than its decomposition temperature. Therefore, when an energy-sensitive resin composition comprising such a compound (A) is heated to a temperature high than the decomposition temperature of the compound (A), even if the heating temperature is low, for instance, 220° C. or lower, ring closure of the polyamic acid in the energy-sensitive resin composition is accelerated not only by the base which is generated by the decomposition of the compound (A), but also by heating itself. As a result, the polyimide resin is formed. Since the compound (A) is sufficiently decomposed by the heating described above, an amount of the remaining compound (A) in the resulting polyimide resin is suppressed to be low. Therefore, when the polyimide resin is heated to a high temperature of, for instance, 300° C. or higher, a reduction in the weight due to the decomposition of the compound (A) is suppressed, which results in good heat resistance.

Further, a compound (A) is preferably such a compound which decomposes by the action of at least light and generates at least one of a base and an acid. In exposing an energy-sensitive resin composition comprising such a compound (A), the compound (A) decomposes in the exposed portions and generates at least one of a base and an acid. The ring closure of the polyamic acid in the energy-sensitive resin composition is accelerated by the base or acid generated in this way so that the exposed portion becomes insoluble in the developing solution. Meanwhile, since the unexposed portion is soluble in the developing solution, it can be removed by dissolving such part in the developing solution. Therefore, it is possible to form a desired pattern by selectively exposing the energy-sensitive resin composition.

Examples of compound (A) include, for instance,
a compound (A-1) which decomposes by the action of at least one of light and heat and generates an imidazole compound, and
an oxime ester compound (A-2). Below, the compounds (A-1) and (A-2) will be explained.

[Compound (A-1) which Decomposes by the Action of at Least One of Light and Heat and Generates an Imidazole Compound]

An imidazole compound which the compound (A-1) generates accelerates ring closure of polyamic acid in the energy-sensitive resin composition according to the present invention as a basic imidation catalyst. The imidazole compound which the compound (A-1) generates may be imidazole or an imidazole compound where a part or all of the hydrogen atoms bound to the carbon atoms in the imidazole are replaced with a substituent(s). The imidazole compound represented by the following formula (3) is preferred.

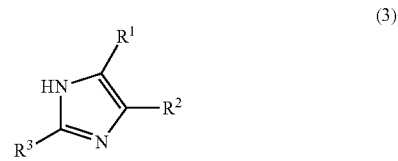

(3)

wherein, $R^1$, $R^2$ and $R^3$ each independently represent a hydrogen atom, a halogen atom, a hydroxyl group, a mercapto group, a sulfide group, a silyl group, a silanol group, a nitro group, a nitroso group, a sulfonato group, a phosphino group, a phosphinyl group, a phosphonato group, or an organic group.

As the organic group in $R^1$, $R^2$, and $R^3$, an alkyl group, an alkenyl group, a cycloalkyl group, a cycloalkenyl group, an aryl group, an aralkyl group, and the like can be exemplified. The organic group may include a hetero atom. In addition, the organic group can be either a straight chain, a branched chain, or cyclic. This organic group is generally monovalent; however, can also be an organic group of divalent or more in a case of forming a cyclic structure or the like.

$R^1$ and $R^2$ can bind to form a cyclic structure, and can further include a hetero atom bond. As the cyclic structure, a heterocycloalkyl group, a heteroaryl group and the like can be exemplified, and the cyclic structure can also be a condensed ring.

In the case where the organic group represented by $R^1$, $R^2$, or $R^3$ includes a hetero atom, examples of the hetero atom include an oxygen atom, a nitrogen atom, and a silicon atom. Specific examples of the bond including a hetero atom include an ether bond, a thioether bond, a carbonyl bond, a thiocarbonyl bond, an ester bond, an amide bond, a urethane bond, an imino bond (—N=C(—R)— or —C(=NR)—: R representing a hydrogen atom or an organic group, the same applies below), a carbonate bond, a sulfonyl bond, a sulfinyl bond, an azo bond and the like. Inter alia, from the viewpoint of thermal resistance of the imidazole compound, an ether bond, a thioether bond, a carbonyl bond, a thiocarbonyl bond, an ester bond, an amide bond, a urethane bond, an imino bond, a carbonate bond, a sulfonyl bond, and a sulfinyl bond are preferable.

A hydrogen atom(s) included in the groups other the organic groups represented by $R^1$, $R^2$, or $R^3$ may be substituted with a hydrocarbon group(s). This hydrocarbon group can be either a straight chain, a branched chain, or cyclic.

As $R^1$, $R^2$, and $R^3$, each independently, a hydrogen atom, an alkyl group having 1 to 12 carbon atoms, an aryl group having 1 to 12 carbon atoms, an alkoxy group having 1 to 12 carbon atoms, and a halogen atom are preferable, and a hydrogen atom is more preferable. Since the imidazole compound where all of $R^1$, $R^2$ and $R^3$ are each a hydrogen atom has a simple structure with a small steric hindrance, such an imidazole compound can easily act on polyamic acid as an imidation catalyst.

The compound (A-1) is not particularly limited, as long as the compound (A-1) decomposes by the action of at least one of light and heat and generates an imidazole compound, preferably an imidazole compound represented by the above formula (3). Compounds which can be used as compound (A-1) are obtained by replacing the skeleton originating from amines which are generated upon exposure from the compounds which are conventionally contained in photosensitive resin compositions and generate amines by the action of light, with the skeleton originating from the imidazole compounds, preferably the imidazole compounds represented by the above formula (3).

Examples of the preferred component (A-1) include the compounds represented by the following formula (4):

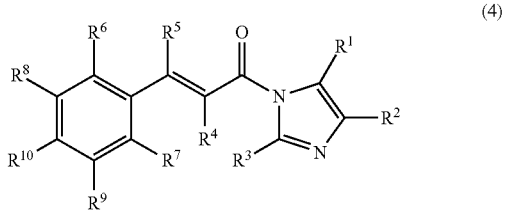

(4)

wherein $R^1$, $R^2$ and $R^3$ each independently represent a hydrogen atom, a halogen atom, a hydroxyl group, a mercapto group, a sulfide group, a silyl group, a silanol group, a nitro group, a nitroso group, a phosphino group, a sulfonato group, a phosphinyl group, a phosphonato group, or an organic group; $R^4$ and $R^5$ each independently represent a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, or an organic group; $R^6$, $R^7$, $R^8$, $R^9$ and $R^{10}$ each independently represent a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group; and two or more of $R^6$, $R^7$, $R^8$, $R^9$ and $R^{10}$ may join together to form a cyclic structure, or may include a bond of a hetero atom.

In the formula (4), $R^1$, $R^2$, and $R^3$ are the same as those explained regarding the formula (3).

In the formula (4), as the organic group represented by $R^4$ and $R^5$, those listed for $R^1$, $R^2$, and $R^3$ can be exemplified. This organic group can include a hetero atom, as in the case of $R^1$, $R^2$, and $R^3$. Further, the organic group can be either a straight chain, a branched chain, or cyclic.

$R^4$ and $R^5$ are preferably, respectively independently a hydrogen atom, an alkyl group having 1 to 10 carbon atoms, a cycloalkyl group having 4 to 13 carbon atoms, a cycloalkenyl group having 4 to 13 carbon atoms, an aryloxy alkyl group having 7 to 16 carbon atoms, an aralkyl group having 7 to 20 carbon atoms, an alkyl group having 2 to 11 carbon atoms substituted with a cyano group, an alkyl group having 1 to 10 carbon atoms substituted with a hydroxyl group, an alkoxy group having 1 to 10 carbon atoms, an amido group having 2 to 11 carbon atoms, an alkylthio group having 1 to 10 carbon atoms, an acyl group having 1 to 10 carbon atoms, an ester group (—COOR, —OCOR: R representing a hydrocarbon group) having 2 to 11 carbon atoms, an aryl group having 6 to 20 carbon atoms, an aryl group having 6 to 20 carbon atoms substituted with an electron donating group and/or an electron withdrawing group, a benzyl group substituted with an electron-donating group and/or an electron withdrawing group, a cyano group, and a methylthio group. More preferably, $R^4$ and $R^5$ are both hydrogen atoms; or $R^4$ is a methyl group and $R^5$ is a hydrogen atom.

In the formula (4), as the organic group in $R^6$, $R^7$, $R^8$, $R^9$ or $R^{10}$, those listed for $R^1$, $R^2$, and $R^3$ can be exemplified. As in the case of $R^1$ and $R^2$, this organic group can include a hetero atom. Further, this organic group can be either a straight chain, a branched chain, or cyclic.

At least two of $R^6$, $R^7$, $R^8$, $R^9$ and $R^{10}$ can bind to form a cyclic structure, and these can further include a bond of hetero atoms. As the cyclic structure, a heterocycloalkyl group, a heteroaryl group and the like can be exemplified, and the cyclic structure can also be a condensed ring. For example, two or more of $R^6$, $R^7$, $R^8$, $R^9$ and $R^{10}$ join together to form a condensed ring such as naphthalene, anthracene, phenanthrene and indene by sharing the atoms of the benzene ring to which $R^6$, $R^7$, $R^8$, $R^9$ and $R^{10}$ are attached.

$R^6$, $R^7$, $R^8$, $R^9$ and $R^{10}$ are preferably, respectively independently a hydrogen atom, an alkyl group having 1 to 10 carbon atoms, a cycloalkyl group having 4 to 13 carbon atoms, a cycloalkenyl group having 4 to 13 carbon atoms, an aryloxy alkyl group having 7 to 16 carbon atoms, an aralkyl group having 7 to 20 carbon atoms, an alkyl group having 2 to 11 carbon atoms substituted with a cyano group, an alkyl group having 1 to 10 carbon atoms substituted with a hydroxyl group, an alkoxy group having 1 to 10 carbon atoms, an amido group having 2 to 11 carbon atoms, an alkylthio group having 1 to 10 carbon atoms, an acyl group having 1 to 10 carbon atoms, an ester group having 2 to 11 carbon atoms, an aryl group having 6 to 20 carbon atoms, an aryl group having 6 to 20 carbon atoms substituted with an electron donating group and/or an electron withdrawing group, a benzyl group substituted with an electron-donating group and/or an electron withdrawing group, a cyano group, a methylthio group and a nitro group.

A case where two or more of $R^6$, $R^7$, $R^8$, $R^9$ and $R^{10}$ join together to form a condensed ring such as naphthalene, anthracene, phenanthrene and indene by sharing the atoms of the benzene ring to which $R^6$, $R^7$, $R^8$, $R^9$ and $R^{10}$ are attached is preferred because the absorption wavelength is shifted toward a longer wavelength.

Among the compounds represented by the above formula (4), compounds represented by the following formula (5);

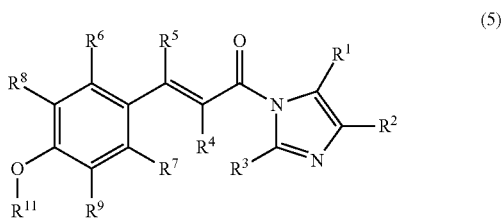

(5)

wherein, $R^1$, $R^2$ and $R^3$ are used synonymously with those in formulas (3) and (4); $R^4$ to $R^9$ are used synonymously with those in formula (4); $R^{11}$ represents a hydrogen atom or an organic group; $R^6$ and $R^7$ shall not be a hydroxyl group; and two or more of $R^6$, $R^7$, $R^8$ and $R^9$ may join together to form a cyclic structure, or may include a bond of a hetero atom, are preferred.

The compounds represented by formula (5) have good solubility in organic solvents because they have a substituent —O—$R^{11}$.

In formula (5), in a case where $R^{11}$ is an organic group, those exemplified with regard to $R^1$, $R^2$ and $R^3$ may be referred to as the organic group. This organic group may include a hetero atom. This organic group may be any of linear, branched, or cyclic. For $R^{11}$, a hydrogen atom or an alkyl group having 1 to 12 carbon atoms is preferred, and a methyl group is more preferred.

Examples of the preferred compounds (A-1) also include the compounds represented by the following formula (6).

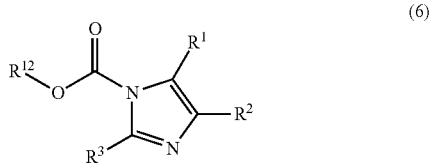

(6)

wherein $R^1$, $R^2$ and $R^3$ each independently represent a hydrogen atom, a halogen atom, a hydroxyl group, a mercapto group, a sulfide group, a silyl group, a silanol group, a nitro group, a nitroso group, a phosphino group, a sulfonato group, a phosphinyl group, a phosphonato group, or an organic group; and $R^{12}$ represents an optionally substituted hydrocarbon group.

$R^1$, $R^2$ and $R^3$ in the formula (6) are the same as those explained with respect to the formula (3).

In the formula (6), examples of $R^{12}$ include an alkyl group having 1 to 20 carbon atoms, an alkenyl group having 2 to 20 carbon atoms, an optionally substituted aryl group having 6 to 20 carbon atoms, and an optionally substituted aralkyl group having 7 to 20 carbon atoms, and an optionally substituted aralkyl group having 7 to 20 carbon atoms is preferred. In a case where the aryl group or an aralkyl group is substituted, examples of the substituent include a halogen atom, a nitro group, an alkyl group having 1 to 4 carbon atoms, and an alkoxy group having 1 to 4 carbon atoms.

The compound represented by the formula (6) can be synthesized by the reaction of an imidazole compound represented by the formula (3) and chloroformate represented by the following formula (7), by the reaction of an imidazole compound represented by the formula (3) and dicarbonate represented by the following formula (8), or by the reaction of a carbonylimidazole compound represented by the following formula (9) and an alcohol represented by the following formula (10).

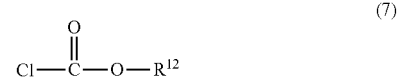

(7)

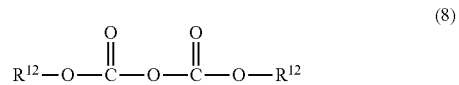

(8)

(9)

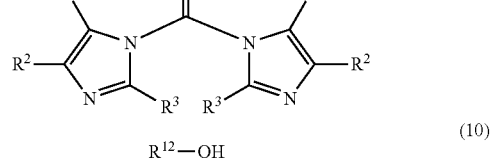

(10)

wherein, $R^1$, $R^2$ and $R^3$ in the formulas (7) to (10) are as defined in the formula (3); and $R^{12}$ is as defined in the formula (6).

Specific examples of the particularly suitable compounds as the compound (A-1) are shown below.

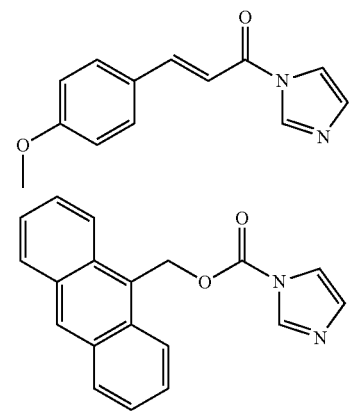

[Oxime Ester Compound (A-2)]

The oxime ester compound (A-2) decomposes by the action of at least one of light and heat and generates at least one of a base and an acid. The ring closure of the polyamic acid in the energy-sensitive resin composition according to the present invention is accelerated by the base or acid generated by the decomposition of compound (A-2).

Examples of the preferred compound (A-2) include compounds represented by the following formula (11).

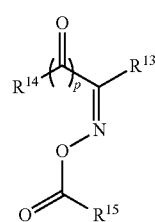

(11)

wherein $R^{13}$ represents an alkyl group having 1 to 10 carbon atoms, an optionally substituted phenyl group or an optionally substituted carbazolyl group; and p is 0 or 1. $R^{14}$ represents an optionally substituted alkyl group having 1 to 10 carbon atoms or an optionally substituted phenyl group. $R^{15}$ represents a hydrogen atom, an alkyl group having 1 to 6 carbon atoms or an optionally substituted phenyl group.

In a case where $R^{13}$ represents an alkyl group having 1 to 10 carbon atoms, the alkyl group may be a straight or branched chain. In this case, the number of carbon atoms of the alkyl group is preferably 1 to 8, and more preferably 1 to 5.

In a case where $R^{13}$ represents an optionally substituted phenyl group, there is no particular limitation for the type of substituents as long as they do not interfere with the object of the present invention. Suitable examples of the substituents which a phenyl group may have include an alkyl group, an alkoxy group, a cycloalkyl group, a cycloalkoxy group, a saturated aliphatic acyl group, an alkoxycarbonyl group, a saturated aliphatic acyloxy group, an optionally substituted phenyl group, an optionally substituted phenoxy group, an optionally substituted benzoyl group, an optionally substituted phenoxycarbonyl group, an optionally substituted benzoyloxy group, an optionally substituted phenylalkyl group, an optionally substituted naphthyl group, an optionally substituted naphthoyl group, an optionally substituted naphthoxycarbonyl group, an optionally substituted naphthoyloxy group, an optionally substituted naphthylalkyl group, an optionally substituted heterocyclyl group, an amino group, an amino group substituted with one or two organic groups, a morpholin-1-yl group, and a piperazin-1-yl group, halogen, a nitro group, and a cyano group and the like. When $R^{13}$ is an optionally substituted phenyl group, and the phenyl group has two or more substituents, the two or more substituents may be the same, or may be different.

In a case where a substituent on the phenyl group is an alkyl group, the number of carbon atoms of the substituent is preferably 1 to 20, more preferably 1 to 10, still more preferably 1 to 6, particularly preferably 1 to 3, and the most preferably 1. The alkyl group may be linear chain or branched. In a case where the substituent on the phenyl group is an alkyl group, specific examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group and the like. The alkyl group may include an ether bond (—O—) in the carbon chain. In this case, examples of the substituent on the phenyl group include an alkoxyalkyl group and an alkoxyalkoxyalkyl group. In a case where the substituent on the phenyl group is an alkoxyalkyl group, a group represented by —$R^{16}$—O—$R^{17}$ is preferred. $R^{16}$ is an alkylene group having 1 to 10 carbon atoms, which may be straight chain or branched chain. $R^{17}$ is an alkyl group having 1 to 10 carbon atoms, which may be straight chain or branched chain. The number of carbon atoms of $R^{16}$ is preferably 1 to 8, more preferably 1 to 5, and particularly preferably 1 to 3. The number of carbon atoms of $R^{17}$ is preferably 1 to 8, more preferably 1 to 5, particularly preferably 1 to 3, and the most preferably, 1. Examples of the alkoxy group having an ether bond in the carbon chain include a methoxyethyl group, an ethoxyethyl group, a methoxyethoxyethyl group, an ethoxyethoxyethyl group, a propyloxyethoxyethyl group, a methoxypropyl group and the like.

In a case where a substituent on the phenyl group is an alkoxy group, the number of carbon atoms of the substituent is preferably 1 to 20, more preferably 1 to 6. The alkoxy group may be linear chain or branched. In a case where a substituent on the phenyl group is an alkoxy group, specific examples of the alkoxy group include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, an isodecyloxy group and the like. The alkoxy group may include an ether bond (—O—) in the carbon chain. Examples of the alkoxy group having an ether bond in the carbon chain include a methoxyethoxy group, an ethoxyethoxy group, a 2-methoxy-1-methylethoxy group, a methoxyethoxyethoxy group, an ethoxyethoxyethoxy group, a propyloxyethoxyethoxy group, a methoxypropyloxy group and the like.

In a case where a substituent on the phenyl group is a cycloalkyl group or a cycloalkoxy group, the number of carbon atoms of the substituent is preferably 3 to 10, more preferably 3 to 6. In a case where a substituent on the phenyl group is a cycloalkyl group, specific examples of the cycloalkyl group include a cyclopropyl group, a cyclobutyl group, a cyclopentyl group, a cyclohexyl group, a cycloheptyl group, a cyclooctyl group and the like. In a case where a substituent on the phenyl group is a cycloalkoxy group, specific examples of the cycloalkoxy group include a cyclopropyloxy group, a cyclobutyloxy group, a cyclopentyloxy group, a cyclohexyloxy group, a cycloheptyloxy group, a cyclooctyloxy group and the like.

In a case where a substituent on the phenyl group is a saturated aliphatic acyl group or a saturated aliphatic acyloxy group, the number of carbon atoms of the substituent is preferably 2 to 20, more preferably 2 to 7. In a case where a substituent on the phenyl group is a saturated aliphatic acyl group, specific examples of the saturated aliphatic acyl group include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, an n-hexadecanoyl group and the like. In a case where a substituent on the phenyl group is a saturated aliphatic acyloxy group, specific examples of the saturated aliphatic acyloxy group include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, an n-hexadecanoyloxy group and the like.

In a case where a substituent on the phenyl group is an alkoxycarbonyl group, the number of carbon atoms of the substituent is preferably 2 to 20, more preferably 2 to 7. In a case where a substituent on the phenyl group is an alkoxycarbonyl group, specific examples of the alkoxycarbonyl group include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, an isodecyloxycarbonyl group and the like.

In a case where a substituent on the phenyl group is a phenylalkyl group, the number of carbon atoms of the substituent is preferably 7 to 20, more preferably 7 to 10. In a case where a substituent on the phenyl group is a naphthylalkyl group, the number of carbon atoms of the substituent is preferably 11 to 20, more preferably 11 to 14. In a case where a substituent on the phenyl group is a phenylalkyl group, specific examples of the phenylalkyl group include a benzyl group, a 2-phenylethyl group, a 3-phenylpropyl group and a 4-phenylbutyl group. In a case where a substituent on the phenyl group is a naphthylalkyl group, specific examples of the naphthylalkyl group include an α-naphthylmethyl group, a β-naphthylmethyl group, a 2-(α-naphthyl)ethyl group and a 2-(β-naphthyl)ethyl group. In a case where a substituent on the phenyl group is a phenylalkyl group or a naphthylalkyl group, the substituent may further have a substituent on the phenyl group or the naphthyl group.

In a case where a substituent on the phenyl group is a heterocyclyl group, the heterocyclyl group is a 5 or 6-membered monocyclic ring having one or more N, S and O, or a heterocyclyl group in which the above monocyclic rings are condensed together, or the above monocyclic ring and a benzene ring are condensed. In a case where the heterocyclyl group is a condensed ring, the number of rings shall be up to 3. Heterocyclic rings contained in the above heterocyclyl group include furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzimidazole, benzotriazole, benzoxazole, benzothiazole, carbazole, purine, quinoline, isoquinoline, quinazoline, phthalazine, cinnoline, quinoxaline and the like. In a case where a substituent on the phenyl group is a heterocyclyl group, the heterocyclyl group may further have a substituent.

In a case where a substituent on the phenyl group is an amino group substituted with one or two organic groups, suitable examples of the organic group include an alkyl group having 1 to 20 carbon atoms, a cycloalkyl group having 3 to 10 carbon atoms, a saturated aliphatic acyl group having 2 to 20 carbon atoms, a saturated aliphatic acyloxy group having 2 to 20 carbon atoms, an optionally substituted phenyl group, an optionally substituted benzoyl group, an optionally substituted phenylalkyl group having 7 to 20 carbon atoms, an optionally substituted naphthyl group, an optionally substituted naphthoyl group, an optionally substituted naphthylalkyl group having 11 to 20 carbon atoms, a heterocyclyl group and the like. Specific examples of these suitable organic groups similarly include those described for the substituents on the phenyl group. Specific examples of the amino group substituted with one or two organic groups include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, a propanoylamino group, an n-butanoylamino group, n-pentanoylamino group, an n-hexanoylamino group, an n-heptanoylamino group, an n-octanoylamino group, an n-decanoylamino group, a benzoylamino group, an α-naphthoylamino group, a β-naphthoylamino group, N-acetyl-N-acetyloxyamino group, and the like.

In a case where the phenyl group, the naphthyl group and the heterocyclyl group included in the substituent on the phenyl group further have a substituent, examples of the substituent include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a monoalkylamino group having an alkyl group with 1 to 6 carbon atoms, a dialkylamino group having alkyl groups with 1 to 6 carbon atoms, a morpholin-1-yl group, a piperazin-1-yl group, halogen, a nitro group, a cyano group and the like. In a case where the phenyl group, the naphthyl group and the heterocyclyl group included in the substituent on the phenyl group further have a substituent, the number of the substituent is preferably, but not limited to, 1 to 4 as long as it does not interfere with the object of the present invention. In a case where the phenyl group, the naphthyl group and the heterocyclyl group included in the substituent on the phenyl group have two or more substituents, the two or more substituents may be the same, or may different.

As described above, whereas explanation was given with respect to the substituents in a case where $R^{13}$ is an optionally substituted phenyl group, among these substituents, alkyl groups, alkoxy groups or alkoxyalkyl groups are preferred.

In a case where $R^{13}$ is an optionally substituted phenyl group, there is no particular limitation for the number of substituents and a position at which a substituent is attached as long as they do not interfere with the object of the present invention. In a case where $R^{13}$ is an optionally substituted phenyl group, the optionally substituted phenyl group is preferably an optionally substituted o-tolyl group in view of excellent efficacy of base generation.

$R^{13}$ is a carbazolyl group which may have a substituent, there is no particular limitation on the type of the substituent, as long as it does not interfere with the object of the present invention. Examples of suitable substituents which the carbazolyl group may have on the carbon atom include an alkyl group having 1 to 20 carbon atoms, an alkoxy group having 1 to 20 carbon atoms, a cycloalkyl group having 3 to 10 carbon atoms, a cycloalkoxy group having 3 to 10 carbon atoms, a saturated aliphatic acyl group having 2 to 20 carbon atoms, an alkoxycarbonyl group having 2 to 20 carbon atoms, a saturated aliphatic acyloxy group having 2 to 20 carbon atoms, an optionally substituted phenyl group, an optionally substituted phenoxy group, an optionally substituted phenylthio group, an optionally substituted phenylcarbonyl group, an optionally substituted benzoyl group, an optionally substituted phenoxycarbonyl group, an optionally substituted benzoyloxy group, an optionally substituted phenylalkyl group having 7 to 20 carbon atoms, an optionally substituted naphthyl group, an optionally substituted naphthoxy group, an optionally substituted naphthylcarbonyl group, an optionally substituted naphthoyl group, an optionally substituted naphthoxycarbonyl group, an optionally substituted naphthoyloxy group, an optionally substituted naphthylalkyl group having 11 to 20 carbon atoms, an optionally substituted heterocyclyl group, an optionally substituted heterocyclylcarbonyl group, an amino group, an amino group substituted with one or two organic groups, a morpholin-1-yl group, a piperazin-1-yl group, halogen, a nitro group, a cyano group and the like.

In a case where $R^{13}$ is an optionally substituted carbazolyl group, examples of suitable substituent which the carbazolyl group may have on the nitrogen atom include an alkyl group having 1 to 20 carbon atoms, a cycloalkyl group having 3 to 10 carbon atoms, a saturated aliphatic acyl group having 2 to 20 carbon atoms, an alkoxycarbonyl group having 2 to 20 carbon atoms, an optionally substituted phenyl group, an optionally substituted benzoyl group, an optionally substituted phenoxycarbonyl group, an optionally substituted phenylalkyl group having 7 to 20 carbon atoms, an optionally substituted naphthyl group, an optionally substituted naphthoyl group, an optionally substituted naphthoxycarbonyl group, an optionally substituted naphthylalkyl group having 11 to 20 carbon atoms, an optionally substituted heterocyclyl group, an optionally substituted heterocyclylcarbonyl group and the like. Among these substituents, an alkyl group having 1 to 20 carbon atoms is preferred, and an alkyl group having 1 to 6 carbon atoms is more preferred, and in particular an ethyl group is particularly preferred.

For an alkyl group, an alkoxy group, a cycloalkyl group, a cycloalkoxy group, a saturated aliphatic acyl group, an alkoxycarbonyl group, a saturated aliphatic acyloxy group, an optionally substituted phenylalkyl group, an optionally substituted naphthylalkyl group, an optionally substituted heterocyclyl group, and an amino group substituted with one or two organic groups, specific examples of the substituents on the carbazolyl group are similar to the examples of the substituents on the phenyl group in a case where $R^{13}$ is an optionally substituted phenyl group.

In a case where the phenyl group, the naphthyl group and the heterocyclyl group included in the substituent on the carbazolyl group in $R^{13}$ further have a substituent, examples of the substituent include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a phenyl group, a naphthyl group, a benzoyl group, a naphthoyl group, a benzoyl group substituted with a group selected from the group consisting of an alkyl group having 1 to 6 carbon atoms, a morpholin-1-yl group, a piperazin-1-yl group and a phenyl group, a monoalkylamino group having an alkyl group with 1 to 6 carbon atoms, a dialkylamino group having alkyl groups with 1 to 6 carbon atoms, a morpholin-1-yl group, a piperazin-1-yl group, halogen, a nitro group, a cyano group and the like. In a case where the phenyl group, the naphthyl group and the heterocyclyl group included in the substituent on the carbazolyl group further have a substituent, the number of the substituent is preferably, but not limited to, 1 to 4 as long as it does not interfere with the object of the present invention. In a case where the phenyl group, the naphthyl group and the heterocyclyl group have two or more substituents, the two or more substituents may be the same, or may be different.

$R^{14}$ is an optionally substituted alkyl group having 1 to 10 carbon atoms or an optionally substituted phenyl group.

In a case where $R^{14}$ is an optionally substituted alkyl group having 1 to 10 carbon atoms, the alkyl group may be a straight or branched chain. In this case, the number of carbon atoms of the alkyl group is preferably 1 to 8, and more preferably 1 to 5.

In $R^{14}$, the substituents on the alkyl group or the phenyl group are not particularly limited as long as they do not interfere with the object of the present invention.

Examples of suitable substituents which the alkyl group may have on the carbon atom include an alkoxy group having 1 to 20 carbon atoms, a cycloalkyl group having 3 to 10 carbon atoms, a cycloalkoxy group having 3 to 10 carbon atoms, a saturated aliphatic acyl group having 2 to 20 carbon atoms, an alkoxycarbonyl group having 2 to 20 carbon atoms, a saturated aliphatic acyloxy group having 2 to 20 carbon atoms, an optionally substituted phenyl group, an optionally substituted phenoxy group, an optionally substituted phenylthio group, an optionally substituted benzoyl group, an optionally substituted phenoxycarbonyl group, an optionally substituted benzoyloxy group, an optionally substituted phenylalkyl group having 7 to 20 carbon atoms, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group having 11 to 20 carbon atoms, an optionally substituted heterocyclyl group, an optionally substituted heterocycly carbonyl group, an amino group, an amino group substituted with one or two organic groups, a morpholin-1-yl group, and a piperazin-1-yl group, halogen, a nitro group, and a cyano group and the like.

Examples of suitable substituents which a phenyl group may have on its carbon atom include an alkyl group having 1 to 20 carbon atoms, in addition to the groups exemplified in the above as the suitable substituents which an alkyl group may have on its carbon atom.

For an alkyl group, an alkoxy group, a cycloalkyl group, a cycloalkoxy group, a saturated aliphatic acyl group, an alkoxycarbonyl group, a saturated aliphatic acyloxy group, an optionally substituted phenylalkyl group, an optionally substituted naphthylalkyl group, an optionally substituted heterocyclyl group, and an amino group substituted with one or two organic groups, specific examples of the substituents on the alkyl group or on the phenyl group are similar to the examples of the substituents on the phenyl group in a case where $R^{13}$ is an optionally substituted phenyl group.

In a case where the phenyl group, the naphthyl group and the heterocyclyl group included in the substituent on the alkyl group or the phenyl group in $R^{14}$ further have a substituent, examples of the substituent include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a phenyl group, a naphthyl group, a benzoyl group, a naphthoyl group, a benzoyl group substituted with a group selected from the group consisting of an alkyl group having 1 to 6 carbon atoms, a morpholin-1-yl group, a piperazin-1-yl group and a phenyl group, a monoalkylamino group having an alkyl group with 1 to 6 carbon atoms, a dialkylamino group having alkyl groups with 1 to 6 carbon atoms, a morpholin-1-yl group, a piperazin-1-yl group, halogen, a nitro group, a cyano group. In a case where the phenyl group, the naphthyl group and the heterocyclyl group included in the substituent on the alkyl group or the phenyl group further have a substituent, the number of the substituent is preferably, but not limited to, 1 to 4 as long as it does not interfere with the object of the present invention. In a case where the phenyl group, the naphthyl group and the heterocyclyl group have two or more substituents, the two or more substituents may be the same, or may be different.

From a viewpoint of efficiency of base generation of the compounds represented by formula (11), as $R^{13}$, the groups represented by the following formula (12):

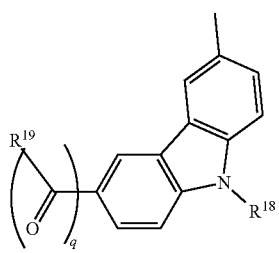

(12)

are preferred. As $R^{14}$, the groups represented by the following formula (13):

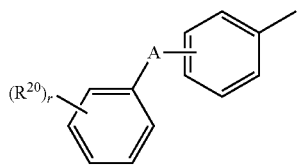

(13)

are preferred.

In formula (12), $R^{18}$ and $R^{19}$ each are a monovalent organic group, and q is 0 or 1. In formula (13), $R^{20}$ is a group selected from the group consisting of a monovalent organic group, an amino group, halogen, a nitro group and a cyano group; A is S or O; and r is an integer between 0 and 4.

$R^{18}$ in the formula (12) can be selected from various kinds of organic groups as far as objects of the present invention are not inhibited. Suitable examples of $R^{18}$ include an alkyl group having 1 to 20 carbon atoms, a cycloalkyl group having 3 to 10 carbon atoms, a saturated aliphatic acyl group having 2 to 20 carbon atoms, an alkoxycarbonyl group having 2 to 20 carbon atoms, an optionally substituted phenyl group, an optionally substituted benzoyl group, an optionally substituted phenoxycarbonyl group, an optionally substituted phenylalkyl group having 7 to 20 carbon atoms, an optionally substituted naphthyl group, an optionally substituted naphthoyl group, an optionally substituted naphthoxycarbonyl group, an optionally substituted naphthylalkyl group having 11 to 20 carbon atoms, an optionally substituted heterocyclyl group, an optionally substituted heterocyclylcarbonyl group and the like.

In $R^{18}$, an alkyl group having 1 to 20 carbon atoms is preferred, an alkyl group having 1 to 6 carbon atoms is more preferred, and an ethyl group is particularly preferred.

There is no particular limitation for $R^{19}$ in the formula (12) as long as they do not interfere with the object of the present invention, and it can be selected from various organic groups. Specific examples of the suitable group for $R^{19}$ include an alkyl group having 1 to 20 carbon atoms, an optionally substituted phenyl group, an optionally substituted naphthyl group and an optionally substituted heterocyclyl group. Among these groups, as $R^{19}$, an optionally substituted phenyl group and an optionally substituted naphthyl group are more preferred, and a 2-methylphenyl group and a naphthyl group are particularly preferred.

In a case where the phenyl group, the naphthyl group and the heterocyclyl group included in $R^{18}$ or $R^{19}$ further have a substituent, examples of the substituents include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a monoalkylamino group having an alkyl group with 1 to 6 carbon atoms, a dialkylamino group having alkyl groups with 1 to 6 carbon atoms, a morpholin-1-yl group, a piperazin-1-yl group, halogen, a nitro group, a cyano group and the like. In a case where the phenyl group, the naphthyl group and the heterocyclyl group included in $R^{18}$ or $R^{19}$ further have a substituent, there is no particular limitation for the number of the substituent as long as it does not interfere with the object of the present invention, but it is preferably 1 to 4. In a case where the phenyl group, the naphthyl group and the heterocyclyl group included in $R^{18}$ or $R^{19}$ have two or more substituents, the two or more substituents may be the same, or may be different.

In a case where $R^{20}$ in the formula (13) is an organic group, it can be selected from various organic groups, as long as it does not interfere with the object of the present invention. In a case where $R^{20}$ is an organic group in the formula (13), suitable examples include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a phenyl group, a naphthyl group, a benzoyl group, a naphthoyl group, a benzoyl group substituted with a group selected from the group consisting of an alkyl group having 1 to 6 carbon atoms, a morpholin-1-yl group, a piperazin-1-yl group and a phenyl group, a monoalkylamino group having an alkyl group with 1 to 6 carbon atoms, a dialkylamino group having alkyl groups with 1 to 6 carbon atoms, a morpholin-1-yl group, a piperazin-1-yl group, halogen, a nitro group, a cyano group; 2-methylphenylcarbonyl group, 4-(piperazin-1-yl)phenylcarbonyl group, and 4-(phenyl)phenyl carbonyl group.

Among $R^{20}$, a benzoyl group, a naphthoyl group, a benzoyl group substituted with a group selected from the group consisting of an alkyl group having 1 to 6 carbon atoms, a morpholin-1-yl group, a piperazin-1-yl group and a phenyl, a nitro group are preferred, and a benzoyl group, a naphthoyl group, 2-methylphenylcarbonyl group, 4-(piperazin-1-yl)phenylcarbonyl group, and 4-(phenyl)phenyl carbonyl group are more preferred.

Further in the formula (13), r is preferably an integer from 0 to 3, more preferably 0 to 2, and particularly preferably 0 or 1. When r is 1, the position at which $R^{20}$ bonds is preferably the para-position to the bonding through which the phenyl group (to which $R^{20}$ bonds) bonds to a sulfur atom.

$R^{15}$ represents a hydrogen atom, an alkyl group having 1 to 6 carbon atoms or an optionally substituted phenyl group. In a case where $R^{15}$ is an optionally substituted phenyl group, optional substituents on the phenyl group are similar to those in a case where $R^{13}$ is an optionally substituted phenyl group. For $R^{15}$, a methyl group, an ethyl group or a phenyl group is preferred, and a methyl group or a phenyl group is more preferred.

The oxime ester compound represented by the above formula (11) wherein p is 0 can be synthesized, for example, by the method described below. First, a ketone compound represented by $R^{14}$—CO—$R^{14}$ is subjected to oximation with hydroxylamine to obtain an oxime compound represented by $R^{12d}$—(C=N—OH)—$R^{13}$. Subsequently, the resulting oxime compound is acylated with an acid halide represented by $R^{15}$—CO-Hal (Hal represents halogen) or an acid anhydride represented by $(R^{15}CO)_2O$ to obtain an oxime ester compound represented by the above formula (11) wherein p is 0.

The oxime ester compound represented by the above formula (11) wherein p is 1 can be synthesized, for example, by the method described below. First, a ketone compound represented by $R^{14}$—CO—$CH_2$—$R^{13}$ is allowed to react with a nitrous ester in the presence of hydrochloric acid to obtain an oxime compound represented by $R^{14}$—CO—(C=N—OH)—$R^{13}$. Subsequently, the resulting oxime compound is acylated with an acid halide represented by $R^{15}$—CO-Hal (Hal represents halogen) or an acid anhydride represented by $(R^{15}CO)_2O$ to obtain an oxime ester compound represented by the above formula (11) wherein p is 1.

Examples of the compounds represented by the above formula (11) include the compounds represented by the following formula (14).

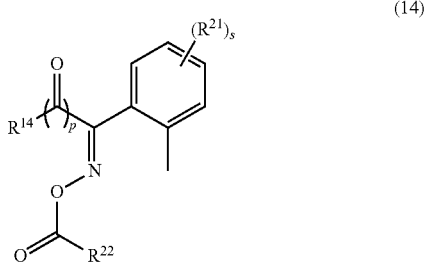

(14)

In the formula (14), p and $R^{14}$ are as defined above. $R^{21}$ is a group selected from the group consisting of a monovalent organic group, an amino group, halogen, a nitro group and a cyano group; s is an integer between 0 and 4; $R^{22}$ represents a hydrogen atom or an alkyl group having 1 to 6 carbon atoms There is no particular limitation for $R^{21}$ in the formula (14), as long as it does not interfere with the object of the present invention, and it can be selected from various organic groups. Preferred examples of $R^{21}$ include an alkyl group, an alkoxy group, a cycloalkyl group, a cycloalkoxy group, a saturated aliphatic acyl group, an alkoxycarbonyl group a saturated aliphatic acyloxy group, an optionally substituted phenyl group, an optionally substituted phenoxy group, an optionally substituted benzoyl group, an optionally substituted phenoxycarbonyl group, an optionally substituted benzoyloxy group, an optionally substituted phenyl-alkyl group, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group, an optionally substituted heterocyclyl group, an amino group, an amino group substituted with one or two organic groups, a morpholin-1-yl group, a piperazin-1-yl group, halogen, a nitro group, a cyano group and the like. In a case where s is an integer of 2 to 4, $R^{21}$ may the same or may be different. Further, the number of carbon atoms of a substituent does not include the number of carbon atoms of another substituent which the substituent further includes.

In a case where $R^{21}$ is an alkyl group, the number of carbon atoms is preferably 1 to 20, and more preferably 1 to 6. Further, in a case where $R^{21}$ is an alkyl group, it may be a straight chain or a branched chain. In a case where $R^{21}$ is an alkyl group, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group and the like. Further, $R^{21}$ is an alkyl group, the alkyl group may include an ether bond (—O—) in the carbon chain. Examples of the alkoxy group having an ether bond in the carbon chain include a methoxyethyl group, an ethoxyethyl group, a methoxyethoxethyl group, an ethoxyethoxyethyl group, a propyloxyethoxyethyl group, a methoxypropyl group and the like.

In a case where $R^{21}$ is an alkoxy group, the number of carbon atoms is preferably 1 to 20, and more preferably 1 to 6. Further, in a case where $R^{21}$ is an alkoxyl group, it may be a straight chain or a branched chain. In a case where $R^{21}$ is an alkoxy group, specific examples include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, an isodecyloxy group and the like. Further, $R^{21}$ is an alkoxy group, the alkoxy group may include an ether bond (—O—) in the carbon chain. Examples of the alkoxy group having an ether bond in the carbon chain include a methoxyethoxy group, an ethoxyethoxy group, a methoxyethoxyethoxy group, an ethoxyethoxyethoxy group, a propyloxyethoxyethoxy group, a methoxypropyloxy group and the like.

In a case where $R^{21}$ is a cycloalkyl group or a cycloalkoxy group, the number of carbon atoms is preferably 3 to 10, and more preferably 3 to 6. In a case where $R^{21}$ is a cycloalkyl group, specific examples include a cyclopropyl group, a cyclobutyl group, a cyclopentyl group, a cyclohexyl group, a cycloheptyl group, a cyclooctyl group and the like. In a case where $R^{21}$ is a cycloalkoxy group, specific examples include a cyclopropyloxy group, a cyclobutyloxy group, a cyclopentyloxy group, a cyclohexyloxy group, a cycloheptyloxy group, a cyclooctyloxy group and the like.

In a case where $R^{21}$ is a saturated aliphatic acyl group or a saturated acyloxy group, the number of carbon atoms is preferably 2 to 20, more preferably 2 to 7. In a case where $R^{21}$ is a saturated aliphatic acyl group, examples include an acetyl group, a propanoyl group, an n-butanoyl group, a 2-methyl propanoyl group, an n-pentanoyl group, a 2,2-dimethyl propanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, an n-hexadecanoyl group and the like. In a case where $R^{21}$ is a saturated aliphatic acyloxy group, examples include an acetyloxy group, a propanoyloxy group, an n-butanoyloxy group, a 2-methyl propanoyloxy group, an n-pentanoyloxy group, a 2,2-dimethyl propanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, an n-hexadecanoyloxy group and the like.

In a case where $R^{21}$ is an alkoxycarbonyl group, number of carbons is preferably 2 to 20, more preferably 2 to 7. In a case where $R^{21}$ is an alkoxycarbonyl group, examples include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, an isodecyloxycarbonyl group and the like.

In a case where $R^{21}$ is a phenyl alkyl group, the number of carbon atoms is preferably 7 to 20, more preferably 7 to 10. Further, in a case where $R^{21}$ is a naphthlalkyl group, the number of carbon atoms is preferably 11 to 20, more preferably 7 to 14. In a case where $R^{21}$ is a phenylalkyl group, specific examples include a benzyl group, 2-phenylethyl group, 3-phenylpropyl group, and 4-phenylbutyl group. In a case where $R^{21}$ is a naphthylalkyl group, specific examples include α-naphthylmethyl group, β-naphthylmethyl group, 2-(α-naphthyl)ethyl group, and 2-(β-naphthyl)ethyl group. In a case where $R^{21}$ is a phenylalkyl group or a naphthylalkyl group, $R^{21}$ may further have a substituent on the phenyl group or the naphthyl group.

In a case where $R^{21}$ is a heterocyclyl group, the heterocyclyl group is a 5 or 6-membered monocyclic ring having one or more N, S or O, or a heterocyclyl group in which the above monocyclic rings are condensed together, or the above monocyclic ring and a benzene ring are condensed. In a case where the heterocyclyl group is a condensed ring, the number of rings shall be up to 3. Heterocyclic rings contained in the above heterocyclyl group include furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzimidazole, benzotriazole, benzoxazole, benzothiazole, carbazole, purine, quinoline, isoquinoline, quinazoline, phthalazine, cinnoline, quinoxaline and the like. In a case where $R^{21}$ is a heterocyclyl group, the heterocyclyl group may further have a substituent.

In a case where $R^{21}$ is an amino group substituted with one or two organic groups, suitable examples of the organic group include an alkyl group having 1 to 20 carbon atoms, a cycloalkyl group having 3 to 10 carbon atoms, a saturated aliphatic acyl group having 2 to 20 carbon atoms, an optionally substituted phenyl group, an optionally substituted benzoyl group, an optionally substituted phenylalkyl group having 7 to 20 carbon atoms, an optionally substituted naphthyl group, an optionally substituted naphthoyl group, an optionally substituted naphthylalkyl group having 11 to 20 carbon atoms, a heterocyclyl group and the like. Specific examples of these preferred organic groups are similar to those of $R^{21}$. Specific examples of the amino group substituted with one or two organic groups include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, a propanoylamino group, an n-butanoylamino group, an n-pentanoylamino group, an n-hexanoylamino group, an n-heptanoylamino group, an n-octanoylamino group, an n-decanoylamino group, a benzoylamino group, an α-naphthoylamino group, a β-naphthoylamino group and the like.

In a case where the phenyl group, the naphthyl group and the heterocyclyl group included in $R^{21}$ further have a substituent, examples of the substituents include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a monoalkylamino group having an alkyl group with 1 to 6 carbon atoms, a dialkylamino group having alkyl groups with 1 to 6 carbon atoms, a morpholin-1-yl group, a piperazin-1-yl group, halogen, a nitro group, a cyano group and the like. In a case where the phenyl group, the naphthyl group and the heterocyclyl group included in $R^{21}$ further have a substituent, there is no particular limitation for the number of the substituent as long as it does not interfere with the object of the present invention, but it is preferably 1 to 4. In a case where the phenyl group, the naphthyl group and the heterocyclyl group included in $R^{21}$ have two or more substituents, the two or more substituents may be the same, or may be different.

Among $R^{21}$, a group selected from the group consisting of an alkyl group having 1 to 6 carbon atoms, an alkoxy group having 1 to 6 carbon atoms, and a saturated aliphatic acyl group having 2 to 7 carbon atoms is preferred, an alkyl group having 1 to 6 carbon atoms is more preferred, and particularly preferred is a methyl group on account of chemical stability and ease of synthesis of an oxime ester compound because of small steric hindrance.

Regarding the position at which $R^{21}$ bonds to a phenyl group, if assuming that the position at which the major skeleton of the oxime ester compound bonds to the phenyl group is position 1 and the position of the methyl group is position 2, the position at which $R^{21}$ bonds to the phenyl group is preferably position 4 or position 5, more preferably position 5. Further, S is preferably an integer 0 to 3, more preferably 0 to 2, and particularly preferably 0 or 1.

$R^{22}$ in the formula (14) represents a hydrogen atom or an alkyl group having 1 to 6 carbon atoms. As $R^{22}$, a methyl group or an ethyl group is preferred and a methyl group is more preferred.

Specific examples of the particularly preferred compounds as the compound (A-2) are shown below.

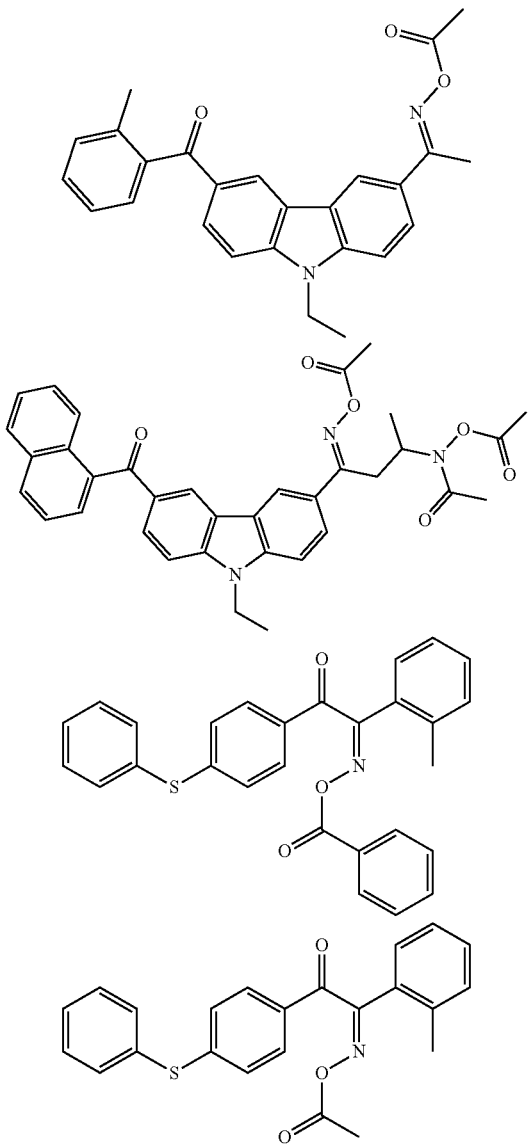

As the compound (A), compounds (A-1) and (A-2) are preferably used in combination. Upon using these compounds in combination, patterning characteristic of the resulting polyimide resins is likely to become particularly good. Inter alia, it is preferred to use the compound E1 in the Examples which is a compound (A-1) and the compound E6 in the Examples which is a compound (A-2).

The content of the compound (A) in the energy-sensitive resin composition is not particularly limited, as far as it does not inhibit the object of the present invention. The content of the compound (A) in the energy-sensitive resin composition is preferably 1 to 50 parts by mass, more preferably 1 to 25 parts by mass, relative to 100 parts by mass of polyamic acid.

Other Components

The energy-sensitive resin composition according to the present invention may comprise components other than the aforementioned components as far as it does not inhibit the object of the present invention. Examples of the other components include surfactants, plasticizers, viscosity modifiers, anti-foaming agents, and colorants.

Method of Manufacturing a Polyimide Film or a Polyimide Molded Product

The method of manufacturing a polyimide film or a polyimide molded product according to the present invention comprises:

a forming step of forming a coating film or a molded product comprising the energy-sensitive composition according to the present invention; and a decomposing step of decomposing the compound (A) in the coating film or the molded product by exposing or heating the coating film or the molded product. Below, each of the steps will be explained.

Forming Step

In the forming step, the energy-sensitive resin composition according to the present invention is applied to the surface of an object to be coated or molded in an appropriate molding method to form a coating film or a molded product. Examples of application methods include a dipping method, a spraying method, a bar coating method, a roll coating method, a spin coating method, and a curtain coating method. The thickness of a coating film is not particularly limited. Typically, the thickness of the coating film is preferably between 2 to 100 µm, and more preferably 3 to 50 µm. The thickness of a coating film can be appropriately controlled by means of application method or by adjusting a solid content or a viscosity of an energy-sensitive resin composition.

After forming the coating film or molded product, the coating film or the molded product may be heated in order to remove the solvent included in the coating film or the molded product. The heating temperature or the heating time is not particularly limited, as far as no heat deterioration or thermal decomposition is caused in the components contained in the energy-sensitive resin composition. In a case where the boiling point of a solvent in the coating film or the molded product is high, the coating film or the molded product may be heated under reduced pressure.

Decomposing Step

In the decomposing step, the coating film or the molded product formed in the forming step is exposed or heated so that the compound (A) in the coating film or the molded product decomposes. The base or acid which generates by the decomposition of the compound (A) accelerates the ring closure of the polyamic acid in the coating film or the molded product. Further, in a case where the coating film or the molded product is heated, the ring closure of the polyamic acid is also accelerated by the heating. As a result of the ring closure of the polyamic acid, a polyimide film or a polyimide molded product is formed.

Examples of radiation used for the exposure of the coating film or the molded product include, for example, ultraviolet rays, electron beams, laser beams and the like emitted from a low-pressure mercury lamp, a high-pressure mercury lamp, a metal halide lamp, a g-line stepper, an i-line stepper and the like. The amount of exposure may vary depending on the light source to be used or the thickness of a coating film and the like, but is usually 1 to 1000 mJ/cm$^2$, and preferably 10 to 500 mJ/cm$^2$.

The heating temperature when the coating film or the molded product is heated is properly controlled depending upon the decomposition temperature of the used compound (A). For instance, the temperature is set to 120 to 350° C., and preferably 150 to 350° C. By heating polyamic acid at a temperature in such a range, it is possible to form a polyimide resin while suppressing the heat deterioration or thermal decomposition of the resulting polyimide resin.

Further, when polyamic acid is heated at a high temperature, a large amount of energy may be consumed or aging deterioration of treatment equipment may be accelerated at a high temperature. Therefore, it is also preferred to heat polyamic acid at relatively low temperatures. Specifically, the upper limit of the temperature at which polyamic acid is heated is preferably 220° C. or lower, more preferably 200° C. or lower, and particularly preferably 190° C. or lower.

Method of Forming a Pattern

In a case where the compound (A) is a compound which decomposes by the action of at least light and generates at least one of a base and an acid, the method of forming a pattern according to the present invention comprises:

a forming step of forming a coating film or a molded product comprising the energy-sensitive resin composition according to the present invention;

an exposure step of exposing the coating film or the molded product selectively, a development step of developing the coating film or the molded product after the exposing, and a heating step of heating the coating film or the molded product after the developing.

Forming Step

The forming step in the method of forming patterns is the same as that explained regarding the forming step in the manufacturing step of the polyimide film or the polyimide molded product, except that the compound (A) in the energy-sensitive composition according to the present invention is a compound which decomposes at least by the action of light and generates at least one of a base and an acid.

Exposure Step

In the exposure step, the coating film or the molded product obtained in the forming step is exposed selectively to a predetermined patterns. Selective exposure is generally performed using a mask of predetermined patterns. The radiation used in the exposure or an amount of exposure is the same as that explained regarding the case where the polyimide film or the molded product is exposed in the decomposing step in the method of manufacturing the polyimide film or the polyimide molded product.

Development Step

In the development step, the unexposed portions are removed from the coating film or the molded product which has been exposed selectively to a predetermined pattern in the exposure step, so as to develop the coating film or the molded product. The unexposed portions are usually removed by dissolving in an alkaline developing solution. Examples of developing methods include a shower developing method, a spray developing method, a dipping developing method, and a paddle developing method. As an alkaline developing solution, an aqueous solution containing one or more alkali compounds selected from inorganic alkali compounds and organic alkali compounds can be used. The concentration of an alkali compound in a developing solution is not particularly limited, as long as the developing solution can satisfactorily develop a coating film or a molded product after the exposing. Typically, the concentration of an alkali compound in a developing solution is preferably between 1 and 10% by mass.

Examples of the inorganic alkali compounds include lithium hydroxide, sodium hydroxide, potassium hydroxide, diammonium hydrogen phosphate, dipotassium hydrogen phosphate, disodium hydrogen phosphate, lithium silicate, sodium silicate, potassium silicate, lithium carbonate, sodium carbonate, potassium carbonate, lithium borate, sodium borate, potassium borate, ammonia and the like. Examples of the organic alkali compounds include tetramethylammonium hydroxide, tetraethylammonium hydroxide, trimethylhydroxyethylammonium hydroxide, methylamine, dimethylamine, trimethylamine, monoethylamine, diethylamine, triethylamine, n-propylamine, di-n-propylamine, isopropylamine, diisopropylamine, methyldiethylamine, dimethylethanolamine, ethanolamine, triethanolamine and the like.

Further, in the developing solution, appropriate amounts of water-soluble organic solvents such as methanol, ethanol, propanol or ethylene glycol, a surfactant, a preservation stabilizer and a resin-dissolution suppressing agent can be added, as needed.

Heating Step

In the heating step, a coating film or a molded product in which unexposed portions have been removed in the development step, so that predetermined patterns have been developed is heated. Thereby, ring closure of polyamic acid which has remained in the coating film or the molded product even after the exposure step is further promoted, so that imidation becomes more sufficient. The heating temperature is similar to the temperature explained for the case where the coating film or the molded product is heated in the decomposing step in the method of manufacturing the polyimide film or the polyimide molded product.

EXAMPLES

Below, the present invention will be described more specifically by way of Examples, but the present invention is not limited to these Examples.

Examples 1 to 16 and Comparative Examples 1 to 3

In the Examples and the Comparative Examples, the tetracarboxylic dianhydrides, the diamines, the solvents, the compounds E1 to E6, and the comparative compounds C1 to C2 shown below were used.

Carboxylic acid anhydride
Tetracarboxylic dianhydride
PMDA: pyromellitic acid dianhydride
s-BPDA: 3,3',4,4'-biphenyltetracarboxylic dianhydride
a-BPDA: 2,3,3',4'-biphenyltetracarboxylic dianhydride
Dicarboxylic acid anhydride
THPA: cis-4-cyclohexene-1,2-dicarboxylic acid anhydride
Diamine
ODA: 4,4'-diaminodiphenyl ether
PPD: p-phenylenediamine
MPD: m-phenylenediamine
2,4-TDA: 2,4-diaminotoluene
BAFL: 9,9-bis(4-aminophenyl) fluorene
BTFL: 9,9-bis(4-amino-3-methylphenyl)fluorene
BisA-P: 4,4'-[1,4-phenylenebis(1-methylethane-1,1-diyl)]dianiline
MDA: 4,4'-diamonodiphenylmethane
Solvent
TMU: N,N,N',N'-tetramethylurea
NMP: N-methyl-2-pyrrolidone
Compounds E1 to E6 and comparative compounds C1 to C2 (In the compound E3 and the comparative compound C2, homochirality of E isomer and Z isomer, respectively, have been obtained.)

Compound E1
Compound E2
Compound E3
Compound E4
Compound E5

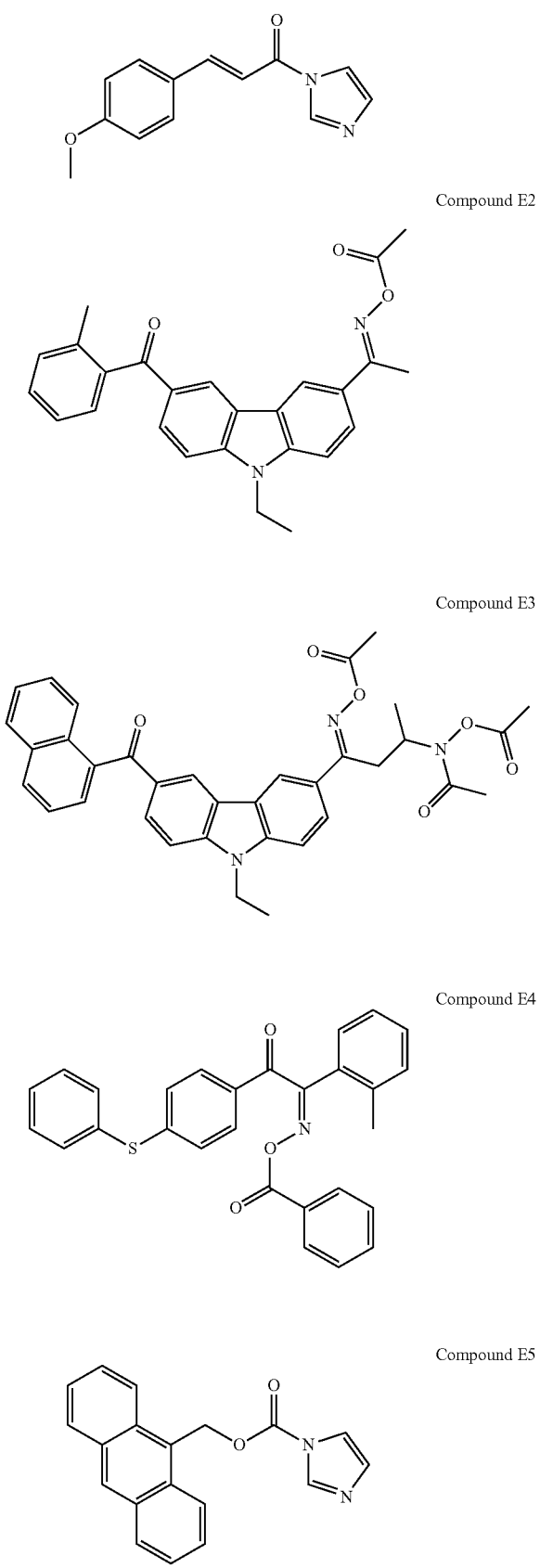

Compound E6
Comparative compound C1
Comparative compound C2

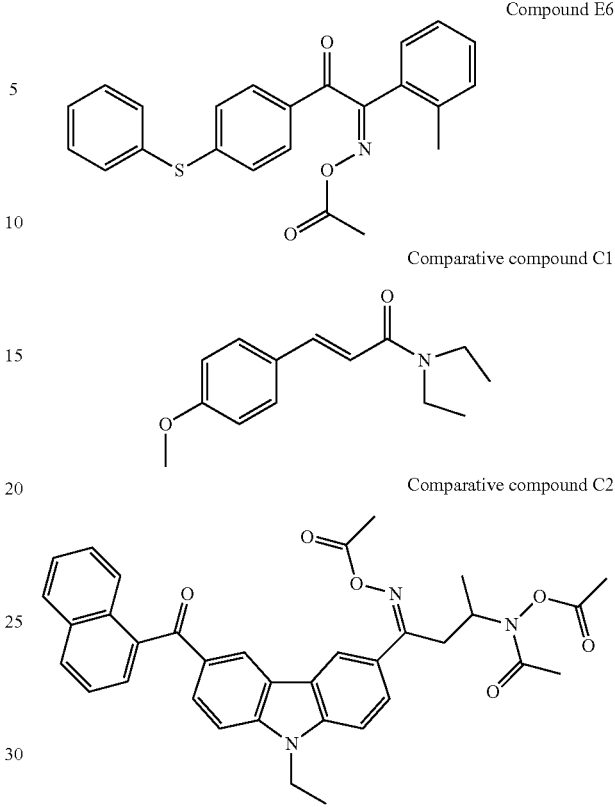

[Preparation of Energy-Sensitive Resin Composition]

To a 5 L separable flask equipped with a stirrer, impellers, a reflux condenser, and a nitrogen gas inlet tube, tetracarboxylic dianhydride, diamine and a solvent of types and amounts mentioned in Tables 1 to 3 were added. Nitrogen gas was introduced into the flask through the nitrogen gas inlet tube to provide the inside of the flask with an atmosphere of nitrogen. Then, the tetracarboxylic dianhydride and the diamine were reacted with each other at 50° C. for 20 hours while stirring the reaction mixture in the flask to obtain a solution of polyamic acid. One of the compounds E1 to E6 and the comparative compounds C1 to C3 in an amount described in Tables 1 to 3 was added to the resulting polyamic acid and stirred to prepare an energy-sensitive resin composition.

[Preparation of Polyimide Film]

A polyimide film was formed by using the resulting energy-sensitive resin composition according to the following method, and the heat resistance, dielectric constant and patterning characteristic of the polyimide films was evaluated.

(Evaluation of Heat Resistance)

The resulting energy-sensitive resin composition was coated on a wafer substrate using a spin coater (manufactured by Mikasa, 1H-360S). The coating film on the wafer substrate was heated at 180° C. for 20 minutes to form a polyimide film with a film thickness of 0.9 μm. From the resulting polyimide film, 5 μg of sample was scraped off for the evaluation of heat resistance. The polyimide resin sample for the evaluation of heat resistance was measured on a differential thermal/thermogravimetry instrument (TG/DTA-6200, manufactured by Seiko Instruments Inc.) in an air flow, at a temperature increasing rate of 10° C./min. to obtain a TG curve. From the resulting TG curve, a 5% thermogravimetric reduction temperature of the sample was obtained. A case where the 5% thermogravimetric reduction temperature was 370° C. or higher was evaluated as excellent (A++); a case where it was 350° C. or higher and lower than 370° C. was evaluated as very good (A+); a case where it was 300° C. or higher and lower than 350° C. was evaluated as good (A); and a case where it was lower than 300° C. was evaluated as bad (B). The results of evaluation of heat resistance are shown in Tables 1 to 3.

(Evaluation of Dielectric Constant)

A resulting energy-sensitive resin composition was coated on a wafer substrate using a spin coater (manufactured by Mikasa, 1H-360S). The coating film on the wafer substrate was heated at 180° C. for 20 min. to form a polyimide film with a film thickness of 0.9 µm. By using the resulting polyimide film as a sample, specific dielectric constant of a polyimide resin was measured on a dielectric constant measuring equipment (SSM-495, manufactured by Semilab Japan KK), at a frequency of 0.1 MHz. A case where the dielectric constant was 3.8 or lower was evaluated as good (A); a case where the dielectric constant was higher than 3.8 and 4.2 or lower was evaluated as slightly bad (B+); and a case where the dielectric constant was higher than 4.2 was evaluated as bad (B). The results of evaluation of dielectric constants are shown in Tables 1 to 3.

(Patterning Characteristic)

The resulting energy-sensitive resin composition was coated on a wafer substrate using a spin coater (manufactured by Mikasa, 1H-360S) and pre-baked at 80° C. for 5 minutes to obtain a coating film with a film thickness of 3 µm. By using a mask with line and space pattern, the coating film was exposed using a high pressure mercury lamp in the condition of 100 mJ/cm$^2$. After the exposed coating film was heated on a hot plate at 120° C. for 5 minutes, the coating film was dipped in a developing solution (a solution in which a 2.38% by mass aqueous solution of tetramethylammonium hydroxide and isopropanol are blended in a ratio of 9:1). As a result, patterns in which the exposed portions, which did not dissolve in the developing solution, remained were obtained. Then, the developed coating film was heated at 180° C. for 1 hour to perform imidation. By observing the coating film after the imidation, the patterning characteristic was evaluated according to the following standards. A case where line with a linewidth of 5 µm could be formed was evaluated as very good (A+); a case where line with a linewidth of 10 µm could be formed was evaluated as good (A); and a case where line with a linewidth of 10 µm could not be formed was evaluated as bad (B). The results of evaluation of patterning characteristic are shown in Tables 1 to 3.

TABLE 1

| | Raw material of polyamic acid solution | | | | Evaluation of polyimide resin | | |
|---|---|---|---|---|---|---|---|
| Example | Carboxylic anhydride (Type/g) | Diamine (Type/g) | Solvent (Type/g) | Compound or comparative compound (Type/g/Decomposing temperature) | Heat resistance | Dielectric constant | Patterning characteristic |
| 1 | PMDA/654.4 | ODA/672.8 | TMU/2951 | E1/158/130° C. | A+ | A | A |
| 2 | PMDA/654.4 | ODA/672.8 | NMP/2518 | E1/158/130° C. | A | A | A |
| 3 | PMDA/654.4 | ODA/672.8 | TMU/2951 | E1/114/130° C. | A+ | A | A |
| 4 | PMDA/654.4 | ODA/672.8 | TMU/2951 | E1/228/130° C. | A+ | A | A |
| 5 | s-BPDA/882.7 | ODA/672.8 | TMU/2951 | E1/158/130° C. | A+ | A | A |
| 6 | a-BPDA/882.7 | ODA/672.8 | TMU/2951 | E1/158/130° C. | A+ | A | A |
| 7 | PMDA/654.4 | PPD/363.4 | TMU/2951 | E1/158/130° C. | A+ | A | A |
| 8 | PMDA/654.4 | MPD/363.4 | TMU/2951 | E1/158/130° C. | A+ | A | A |
| 9 | PMDA/654.4 | 2,4-TDA/410.5 | TMU/2951 | E1/158/130° C. | A+ | A | A |
| 10 | PMDA/654.4 | ODA/672.8 | TMU/2951 | E2/278/170° C. | A+ | A | A |
| 11 | PMDA/654.4 | ODA/672.8 | NMP/2518 | E2/278/170° C. | A | A | A |
| 12 | PMDA/654.4 | ODA/672.8 | TMU/2951 | E3/300/170° C. | A+ | A | A |
| 13 | PMDA/654.4 | ODA/672.8 | TMU/2951 | E4/263/130° C. | A+ | A | A |
| 14 | PMDA/654.4 | ODA/672.8 | TMU/2951 | E5/160/130° C. | A+ | A | A |
| 15 | PMDA/654.4 | ODA/672.0 | TMU/2951 | E6/263/130° C. | A+ | A | A |
| 16 | PMDA/654.4 | ODA/672.8 | TMU/2951 | E1/79/130° C. E2/139/170° C. | A+ | A | A |
| 17 | PMDA/654.4 | ODA/672.8 | NMP/2518 | E1/158/130° C. E6/263/130° C. | A+ | A | A+ |
| 18 | PMDA/654.4 | ODA/672.8 | TMU/2951 | E1/158/130° C. E6/263/130° C. | A+ | A | A+ |
| 19 | s-BPDA/882.7 | ODA/672.8 | NMP/2518 | E1/158/130° C. E6/263/130° C. | A+ | A | A+ |
| 20 | s-BPDA/882.7 | ODA/672.8 | TMU/2951 | E1/158/130° C. E6/263/130° C. | A+ | A | A+ |
| 21 | a-BPDA/882.7 | ODA/672.8 | NMP/2518 | E1/158/130° C. E6/263/130° C. | A+ | A | A+ |
| 22 | a-BPDA/882.7 | ODA/672.8 | TMU/2951 | E1/158/130° C. E6/263/130° C. | A+ | A | A+ |
| 23 | s-BPDA/882.7 | ODA/672.8 | NMP/2518 | E1/158/130° C. | A+ | A | A |
| 24 | a-BPDA/882.7 | ODA/672.8 | NMP/2518 | E1/158/130° C. | A+ | A | A |
| 25 | PMDA/654.4 | PPD/363.4 | TMU/2951 | E1/158/130° C. E6/263/130° C. | A+ | A | A+ |
| 26 | PMDA/654.4 | MPD/363.4 | TMU/2951 | E1/158/130° C. E6/263/130° C. | A+ | A | A+ |
| 27 | PMDA/654.4 | 2,4-TDA/410.5 | TMU/2951 | E1/158/130° C. E6/263/130° C. | A+ | A | A+ |

TABLE 2

| | Raw material of polyamic acid solution | | | Compound or comparative compound | Evaluation of polyimide resin | | |
|---|---|---|---|---|---|---|---|
| | Carboxylic anhydride | Diamine | Solvent | (Type/g/Decomposing | Heat | Dielectric | Patterning |
| Example | (Type/g) | (Type/g) | (Type/g) | temperature) | resistance | constant | characteristic |
| 28 | a-BPDA/882.7 | BAFL/1170.8 | NMP/2518 | E1/158/130° C. E6/263/130° C. | A++ | A | A+ |
| 29 | a-BPDA/882.7 | BAFL/1170.8 | TMU/2951 | E1/158/130° C. E6/263/130° C. | A++ | A | A+ |
| 30 | a-BPDA/882.7 | BAFL/1170.8 | TMU/2951 | E1/158/130° C. | A++ | A | A+ |
| 31 | s-BPDA/882.7 | BAFL/1170.8 | NMP/2518 | E1/158/130° C. E6/263/130° C. | A++ | A | A+ |
| 32 | s-BPDA/882.7 | BAFL/1170.8 | TMU/2951 | E1/158/130° C. E6/263/130° C. | A++ | A | A+ |
| 33 | s-BPDA/882.7 | BAFL/1170.8 | TMU/2951 | E1/158/130° C. | A++ | A | A+ |
| 34 | THPA/228.2 a-BPDA/441.3 | BAFL/1170.8 | NMP/2518 | E1/158/130° C. E6/263/130° C. | A++ | A | A+ |
| 35 | THPA/228.2 a-BPDA/441.3 | BAFL/1170.8 | TMU/2951 | E1/158/130° C. E6/263/130° C. | A++ | A | A+ |
| 36 | THPA/228.2 a-BPDA/441.3 | BAFL/1170.8 | TMU/2951 | E1/158/130° C. | A++ | A | A |
| 37 | THPA/228.2 s-BPDA/441.3 | BAFL/1170.8 | NMP/2518 | E1/158/130° C. E6/263/130° C. | A++ | A | A+ |
| 38 | THPA/228.2 s-BPDA/441.3 | BAFL/1170.8 | TMU/2951 | E1/158/130° C. E6/263/130° C. | A++ | A | A+ |
| 39 | THPA/228.2 s-BPDA/441.3 | BAFL/1170.8 | TMU/2951 | E1/158/130° C. | A++ | A | A |
| 40 | THPA/228.2 a-BPDA/441.3 | BTFL/1265.0 | NMP/2518 | E1/158/130° C. E6/263/130° C. | A++ | A | A+ |
| 41 | THPA/228.2 a-BPDA/441.3 | BTFL/1265.0 | TMU/2951 | E1/158/130° C. E6/263/130° C. | A++ | A | A+ |
| 42 | THPA/228.2 a-BPDA/441.3 | BTFL/1265.0 | TMU/2951 | E1/158/130° C. | A++ | A | A |

TABLE 3

| | Raw material of polyamic acid solution | | | Compound or comparative compound | Evaluation of polyimide resin | | |
|---|---|---|---|---|---|---|---|
| | Carboxylic anhydride | Diamine | Solvent | (Type/g/Decomposing | Heat | Dielectric | Patterning |
| | (Type/g) | (Type/g) | (Type/g) | temperature) | resistance | constant | characteristic |
| Example | | | | | | | |
| 43 | THPA/228.2 s-BPDA/441.3 | BisA-P/1157.5 | NMP/2518 | E1/158/130° C. E6/263/130° C. | A+ | A | A+ |
| 44 | THPA/228.2 s-BPDA/441.3 | BisA-P/1157.5 | TMU/2951 | E1/158/130° C. E6/263/130° C. | A+ | A | A+ |
| 45 | THPA/228.2 s-BPDA/441.3 | BisA-P/1157.5 | TMU/2951 | E1/158/130° C. | A+ | A | A |
| 46 | THPA/228.2 s-BPDA/441.3 | MDA/666.2 | NMP/2518 | E1/158/130° C. E6/263/130° C. | A+ | A | A+ |
| 47 | THPA/228.2 s-BPDA/441.3 | MDA/666.2 | TMU/2951 | E1/158/130° C. E6/263/130° C. | A+ | A | A+ |
| 48 | THPA/228.2 s-BPDA/441.3 | MDA/666.2 | TMU/2951 | E1/158/130° C. | A+ | A | A |
| Comparative Example | | | | | | | |
| 1 | PMDA/654.4 | ODA/672.8 | TMU/2951 | None/0/— | A | B+ | B |
| 2 | PMDA/654.4 | ODA/672.8 | TMU/2951 | C1/158/250° C. | B | B+ | A |
| 3 | PMDA/654.4 | ODA/672.8 | TMU/2951 | C2/250/230° C. | B | B+ | A |

It can be seen from Examples 1 to 16 that even in the case where heat treatment was performed at a low temperature, i.e., 180° C., it was possible to obtain a polyimide resin which had good heat resistance, a low dielectric constant and good patterning characteristic from the energy-sensitive resin composition comprising polyamic acid, by adding the compound (A-1) (in particular, the compound represented by the formula (4) or (6)) which decomposes by the action of at least one of light and heat and generates an imidazole compound or the oxime ester compound (A-2) (in particular, the compound represented by the formula (11)). The compounds E1 to E6 which were used in the Examples 1 to 16 fall under the compounds which decompose at temperatures of from 120 to 180° C. and generate a base.

According to Examples 17 to 48, it can be seen that the patterning characteristic of the polyimide resins tended to become particularly better by using the compound E1, which belongs to the compound (A-1), and the compound E6, which belongs to the compound (A-2), in combination.

According to the Comparative Example 1, it can be seen that, when the compound E1 to E6 were not added, the heat resistance was rather good, but the dielectric constant tended to become higher and therefore, the patterning characteristic was poor.

According to Comparative Examples 2 and 3, it can be seen that in the case where the comparative compound C1 which does not generate an imidazole compound even when decomposing by the action of light or heat or in the case where the comparative compound C2 which is an oxime ester compound but not a compound represented by the formula (11), pattern characteristic was good but the dielectric constant tended to become higher. The comparative compound C1 used in Comparative Example 2 and the comparative compound C2 used in Comparative Example 3 are the compounds which decompose at high temperatures, namely at 250° C. and 230° C., respectively, to generate a base.

What is claimed is:

1. An energy-sensitive resin composition comprising polyamic acid, a solvent, and a compound (A), wherein the polyamic acid is obtained by reacting tetracarboxylic dianhydride with diamine, the compound (A) comprises at least one of:
   a compound (A-1) that decomposes by the action of at least one of light and heat and generates an imidazole compound; and
   an oxime ester compound (A-2),
      wherein the compound (A-1) is represented by the following formula (4) or a compound represented by the following formula (6), and
      the oxime ester compound (A-2) is represented by the following formula (11),

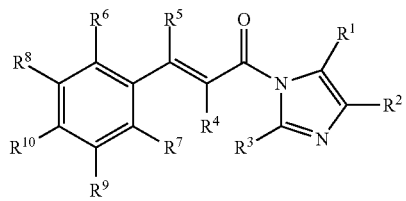

(4)

wherein $R^1$, $R^2$ and $R^3$ each independently represents a hydrogen atom, a halogen atom, a hydroxyl group, a mercapto group, a sulfide group, a silyl group, a silanol group, a nitro group, a nitroso group, a phosphino group, a sulfonato group, a phosphinyl group, a phosphonato group, or an organic group; $R^4$ and $R^5$ each independently represent a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, or an organic group; $R^6$, $R^7$, $R^8$, $R^9$ and $R^{10}$ each independently represent a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group; provided that neither $R^6$ nor $R^7$ is a hydroxyl group; and two or more of $R^6$, $R^7$, $R^8$, $R^9$ and $R^{10}$ optionally join together to form a cyclic structure, or optionally include a bond of a heteroatom;

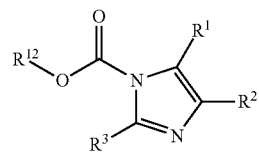

(6)

wherein $R^1$, $R^2$ and $R^3$ each independently represents a hydrogen atom, a halogen atom, a hydroxyl group, a mercapto group, a sulfide group, a silyl group, a silanol group, a nitro group, a nitroso group, a phosphino group, a sulfonato group, a phosphinyl group, a phosphonato group, or an organic group; and $R^{12}$ represents an optionally substituted hydrocarbon group;

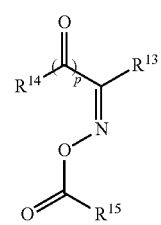

(11)

wherein $R^{13}$ represents an alkyl group having 1 to 10 carbon atoms, an optionally substituted phenyl group or an optionally substituted carbazolyl group; and p is 0 or 1; $R^{14}$ represents an optionally substituted alkyl group having 1 to 10 carbon atoms or an optionally substituted phenyl group; $R^{15}$ represents a hydrogen atom, an alkyl group having 1 to 6 carbon atoms or an optionally substituted phenyl group.

2. The composition according to claim 1, wherein the compound (A) is a compound that decomposes at 120 to 180° C. and generates a base.

3. The composition according to claim 1, wherein the compound (A) is a compound that decomposes by the action of at least light and generates at least one of a base and an acid.

4. The composition according to claim 1 comprising the compound represented by the formula (11), wherein $R^{13}$ of the formula (11) is a group represented by the following formula (12),

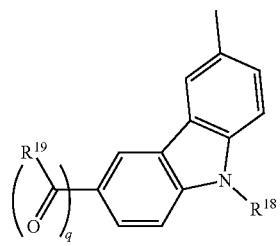

(12)

wherein $R^{18}$ and $R^{19}$ each are a monovalent organic group, and q is 0 or 1.

5. The composition according to claim 1 comprising the compound represented by the formula (11), wherein $R^{14}$ of the formula (11) is a group represented by the following formula (13),

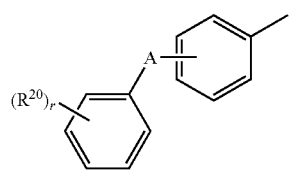

(13)

wherein $R^{20}$ is a group selected from the group consisting of a monovalent organic group, an amino group, halogen, a nitro group and a cyano group; A is S or O; and r is an integer between 0 and 4.

6. The composition according to claim 1 comprising a compound represented by the following formula (5) as the compound represented by the formula (4),

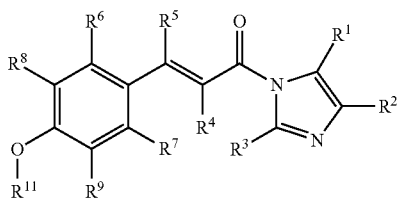

(5)

wherein $R^1$ to $R^9$ are used synonymously with those in formula (4); $R^{11}$ represents a hydrogen atom or an organic group; and two or more of $R^6$, $R^7$, $R^8$ and $R^9$ may join together to form a cyclic structure, or may include a bond of a hetero atom, are preferred.

7. The composition according to claim 1, wherein the solvent is at least one selected from the group consisting of N-methyl-2-pyrrolidone, N,N-dimethylacetamide, N,N-diethyl acetamide, N,N-dimethylformamide, N,N-diethylformamide, N-methylcaprolactam and N,N,N',N'-tetramethylurea.

8. The composition according to claim 1 comprising both of the compound (A-1) and the compound (A-2).

9. The composition according to claim 8, wherein the compound (A-1) is compound E1 and the compound (A-2) is compound E6, both represented by the following formulas

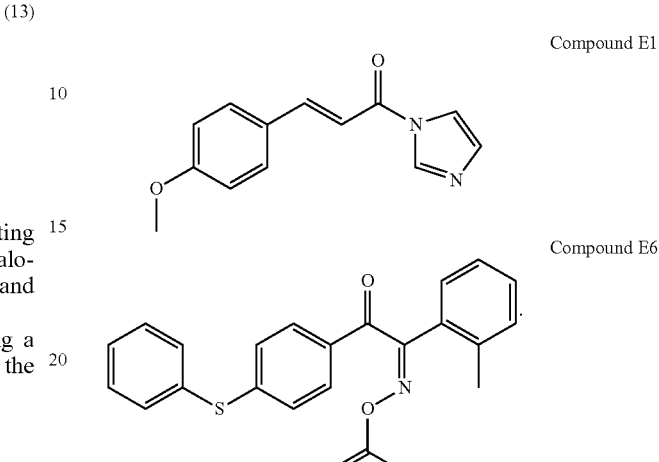

10. A method of manufacturing a polyimide film or a polyimide molded product, comprising:
   forming a coating film or a molded product comprising the composition according to claim 1; and
   decomposing the compound (A) contained in the coating film or the molded product by exposing or heating the coating film or the molded product.

11. A method of forming a pattern, comprising:
   forming a coating film or a molded product comprising the composition according to claim 3;
   selectively exposing the coating film or the molded product;
   developing the coating film or the molded product after the exposing; and
   heating the coating film or the molded product after the developing.

* * * * *

UNITED STATES PATENT AND TRADEMARK OFFICE
CERTIFICATE OF CORRECTION

PATENT NO. : 9,529,258 B2
APPLICATION NO. : 14/758199
DATED : December 27, 2016
INVENTOR(S) : Kunihiro Noda, Hiroki Chisaka and Kazuya Someya It is certified that error appears in the above-identified patent and that said Letters Patent is hereby corrected as shown below:

In the Specification

Column 4, Line 58, "(4-aminophenoxyl)" should be --(4-aminophenoxy)--.

Column 4, Line 59, "aminophenoxyl)" should be --aminophenoxy)--.

Column 4, Line 60, "aminophenoxyl)" should be --aminophenoxy)--.

Column 4, Line 61, "aminophenoxyl)" should be --aminophenoxy)--.

Column 16, Line 39, "heterocycly" should be --heterocyclyl--.

Column 19, Line 56, after "atoms" insert --.--.

Column 20, Line 30, "methoxyethoxethyl" should be --methoxyethoxyethyl--.

Column 21, Line 37, "naphthlalkyl" should be --naphthylalkyl--.

Column 26, Line 60, "diamonodiphenylmethane" should be --diaminodiphenylmethane--.

Column 26, Line 63, "pyrolidone" should be --pyrrolidone--.

Column 29-30, Line 20 (Table 1), "ODA/672.0" should be --ODA/672.8--.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*